United States Patent
Yokoyama et al.

(10) Patent No.: US 8,999,890 B2
(45) Date of Patent: Apr. 7, 2015

(54) SIGNALING COMPOSITIONS, METHODS, AND SYSTEMS FOR EFFECTING PLANT BURNDOWN AND HERBICIDE ENHANCEMENT

(71) Applicant: KamTec, Waverly, NE (US)

(72) Inventors: Henry Yokoyama, Waverly, NE (US);
James H. H. Chan, Waverly, NE (US);
Paul S. Oyama, Waverly, NE (US);
Loren J. Hov, Waverly, NE (US);
Christopher Lee Petersen, Lincoln, NE (US); David Vu, Waverly, NE (US);
John A. Eastin, Waverly, NE (US)

(73) Assignee: Kamtec, LLC, Waverly, NE (US)

( * ) Notice: Subject to any disclaimer, the term of this patent is extended or adjusted under 35 U.S.C. 154(b) by 0 days.

(21) Appl. No.: 13/841,469

(22) Filed: Mar. 15, 2013

(65) Prior Publication Data
US 2014/0283199 A1 Sep. 18, 2014

(51) Int. Cl.
*A01N 25/26* (2006.01)
*A01N 37/10* (2006.01)
*A01N 39/00* (2006.01)
*C12N 15/01* (2006.01)
*A01N 53/00* (2006.01)

(52) U.S. Cl.
CPC ............... *C12N 15/01* (2013.01); *A01N 37/10* (2013.01); *A01N 53/00* (2013.01)

(58) Field of Classification Search
None
See application file for complete search history.

(56) References Cited

U.S. PATENT DOCUMENTS

| | | | |
|---|---|---|---|
| 4,764,201 A | 8/1988 | Iino et al. | |
| 5,710,099 A | 1/1998 | Yokoyama et al. | |
| 8,466,088 B2 * | 6/2013 | Shimoharada et al. | 504/118 |
| 2005/0239652 A1 | 10/2005 | Crockett et al. | |
| 2007/0124839 A1 | 5/2007 | Schulz et al. | |
| 2011/0195841 A1 | 8/2011 | Dittgen et al. | |
| 2011/0207607 A1 * | 8/2011 | Satchivi et al. | 504/105 |

FOREIGN PATENT DOCUMENTS

| | | | |
|---|---|---|---|
| CN | 101027979 | * | 6/2007 |
| CN | 101774852 | * | 7/2010 |
| WO | WO 2008014505 | * | 1/2008 |

OTHER PUBLICATIONS

Liu et al(Studies on the action of DA-6 reducing the phytotoxicity of ethametsulfuron on rice, Xiandai Nongyao, 2005, 4 No. 3, 31-32, 35).*
Yokoyama et al.,Bioregulation of Pigment Biosynthesis, American Chemical Society, 1982, pp. 153-173.*
Poling et al., Chemical Regulation of Carotenoid Biosynthesis. Part 9. Synthetic Regulators of Carotenoid Biosynthesis in Citrus Paradisi, Phytochemistry(Elsevier), 1976, 15(11), 1685-7.*

* cited by examiner

*Primary Examiner* — Alton Pryor
(74) *Attorney, Agent, or Firm* — Suiter Swantz pc llo

(57) ABSTRACT

Bio-regulators from a group of quaternary ammonium moieties modify a gene expression in undesirable plants to inhibit growth and robustness and enhance the effectiveness of herbicides. Such bio-regulator may be applied to plants through seed treatments, root drenching, spraying and dusting, or to soil were desirable crops are planted or will be planted. Bio-regulators may be duel-acting; causing beneficial modification to gene expressions in desirable plants while modifying gene expression in undesirable plants, making them more susceptible to herbicides. Bio-regulators are Ester Compounds, BMIA Compounds or related salts of those compounds.

19 Claims, 10 Drawing Sheets

SIGNALING COMPOSITIONS, METHODS, AND SYSTEMS FOR EFFECTING PLANT BURNDOWN AND HERBICIDE ENHANCEMENT

FIELD OF INVENTION

The present invention relates to bio-regulation in plants, and more particularly to compositions for inducing valuable qualities in plants such as earlier germination, increased vigor, earlier or delayed maturity, improved crop yield, tolerance to biotic and abiotic crop production stresses and enhancement of herbicidal activity.

BACKGROUND

Global food production has increased steadily and yet there are still countries with malnourished populations. Many of these countries rely on agriculture, and have not seen an increase in overall food production in spite of global increases. Some of these countries cannot grow the various foods required to meet nutrition requirements due to human and environmental forces.

With advancements in technology, people live longer, birth rates are higher, and population increases place additional stress on resources. As the population continues to increase, so will the demand for food, fiber, and agriculture based renewable energy sources. With an increased population comes the requirement for additional housing and infrastructure. This increase decreases the amount of acreage available for effective crop production. Therefore, there is an increasing demand for agricultural crop products, while the available land to produce such products is limited. Other concerns include depletion of nutrients from the available soil, the effectiveness of current agricultural production methods, environmental impacts on plants, and loss of arable land resulting from increased global warming (which has yet to be adequately studied).

With these growing concerns, it is necessary for society to continually develop advancements in sustainably increasing production from limited arable resources. It is also evident that cost effective methods for increased agricultural production and crop yield must undergo continued development.

Attempts to address some of these problems have included methods such as breeding and selecting more productive plant varieties; improved crop management; advances in technology; use of fertilizers, herbicides, and pesticides; and changes in irrigation techniques. These methods have been useful in some countries, but have had limited impact on developing nations where cultural practices and farm management are not advanced and where the cost of fertilizer or lack of irrigation practices have produced less than satisfactory crop yields. Even in countries with advanced farm management techniques, such as the United States, continual advances in productivity are necessary, and such necessity may not be satisfied by known compositions and methods.

Genetic engineering techniques are being employed to produce plants that are tolerant or resistant to environmental stresses and pathogen and pest pressure (abiotic and biotic stresses, respectively). Genetic engineering of plants for crop production often involves identification and insertion of foreign genes. The practice is time consuming, costly and often limiting with regards to numbers of genes that can be inserted or activated in a genetically engineered plant.

Insufficient time and attention has been devoted to the control of stress in biological processes at the cellular level. Stress is relevant to crop productivity and quality. Plants have the biological potential to deal with environmental stress in a fashion which may be exploited for the sustainable benefit of humankind. Compositions and methods for using such compositions to modify gene expression in plants to improve crop yields under various environmental stresses are needed.

SUMMARY OF THE INVENTION

Accordingly, it is an object of the present invention to provide a novel method for manipulating the levels of gene products that are involved in persistence of useful and elimination of non-useful plants in the presence and absence of abiotic and biotic stresses.

It is another object of the present invention to provide the procedures necessary for performing the manipulations.

It is still another object of the present invention to provide the necessary components for inducing the manipulated stress levels.

It is still another object of the present invention to develop inexpensive methods and procedures that can be produced on large and small scales.

It is still another object of the present invention to provide appropriate compositions and families of compositions to be incorporated into the methods and procedures.

It is still another object of the present invention to provide appropriate wetting agents and penetrating adjuvants to be used in the methods and procedures.

It is still another object of the present invention to provide bio-regulator solutions formed from mixing amounts of said compositions and appropriate wetting agents and penetrating adjuvants to be used in the methods and procedures.

It is still another object of the present invention to provide various methods of applying said compositions to sexual and vegetative parts of plants and to microorganisms.

In accordance with the above objects of the invention, in one embodiment of the present invention, several families of compositions are applied according to the methods and procedures outlined. The compositions are applied in bio-regulatory active concentrations to seeds and/or plants, sufficient to utilize, enhance or inhibit internal and external plant characteristics, even while the plant may be subjected to various stress conditions such as high insect and microbial pests, saline environments, anaerobic environments, high temperatures, low temperatures and drought conditions. Some of the internal characteristics utilized, enhanced or inhibited include, but are not limited to, abiotic and biotic stress response gene products, sugar, essential oil, Vitamin C, carotenoids and protein content. Some external characteristics utilized, enhanced or inhibited include, but are not limited to, vigor, pigment accumulation, rate of development, and yield.

In another embodiment, the compositions keep the plants in a bio-regulated state sufficient to increase or enhance the treated plants ability to grow. The applied compositions are selected from the group of chemical compounds represented by the formula:

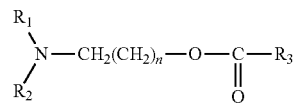

wherein R1 and R2 are preferably lower alkyl groups containing one to six carbon atoms, inclusive, or a benzyl substituent each of identical or dissimilar structure; n is an integer (preferably from zero to four); R3 is selected from the group comprising lower alkyl compositions containing from one to six carbon atoms (preferably including cyclopropyl, phenyl, and alkyl substituted phenyl). This family of compositions is referred to herein as the "Ester Compounds" and may also include acid addition salts of such compounds.

In another embodiment, the applied compositions are selected from the group represented by the formula:

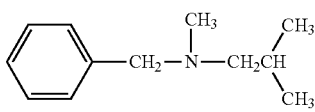

or a substantially similar molecules. This family of compounds, as more fully defined herein, is referred to herein as the "BMIA Compounds".

In another embodiment, the applied compositions are also selected from the group of salts resulting from the Ester Compounds and BMIA Compounds (preferably salts resulting from halides—i.e. chloro and bromo salts). This family of compositions is referred to herein as the "Salt Compounds".

In another embodiment the applied compositions are selected from a combination of the Ester Compounds and their Salt Compounds, or from a combination of the BMIA Compounds and their Salt Compounds.

In another embodiment the applied compositions are selected from the previously disclosed groups in bio-regulatory concentrations in combination with herbicide compositions sufficient to decrease or inhibit a treated plant's ability to grow, or to increase the herbicidal activity. In this embodiment the method is preferably used for killing undesirable plants and weeds, such as during burndown.

In another embodiment, amounts of these compositions are applied in bio-regulatory concentrations to form bio-regulator solutions, which are applied according to various means. In another embodiment, the range of concentrations of compositions used to generate the bio-regulator solutions is between 0.05 and 2000 parts per million ("ppm"). Seed treatment solutions may be used in a very low dose total volume, but high A.I. concentration, applications.

In another embodiment, the present invention includes, soaking, spraying, dusting and coating plants and seeds. These application methods may be utilized for both the sexual reproductive and vegetative parts of plants.

In another embodiment, seed treatment includes incorporating the plant bio-regulators into seed priming systems.

In a seed priming system, seeds are partially hydrated and maintained under defined moisture, temperature and aeration conditions for a prescribed period of time. During priming, seed metabolic activity facilitates completion of important pre-germination steps like membrane repair, DNA and RNA synthesis and repair, expression of particular gene products that are involved in seed germination and derived plant development over a range of environments, development of immature embryos, alteration of tissues covering the embryo, and removal of dormancy blocks to advance germination status. After priming, seeds are generally dried back to storage moisture contents so they can be planted with conventional equipment at a later date.

Seeds treated in a priming system have fewer steps to complete than non-primed seeds in order to accomplish germination. Consequently, priming improves the rate and uniformity of seed germination. Additionally, seed repair and/or removal of dormancy blocks during priming of a particular seed lot can result in increased germination percentage. The improvements priming offers to seed germination characteristics often translate to more rapid and uniform seedling emergence, increased uniformity and rates of plant development, and increased yields.

In this embodiment the method is preferably used to enhance or inhibit seed metabolic activity that is made amenable to bio-regulator compound activity as a function of the metabolic status achieved and/or maintained during and/or following the seed priming process to influence seed germination and derived plant growth and development under a range of environments that include the presence and absence of abiotic and/or biotic stress.

In another embodiment, seed treatment includes incorporating the plant bio-regulators into seed coating systems. Seed coating involves application of certain active ingredients, including but not limited to fungicides, insecticides, plant growth promoting compounds, beneficial microbes, to seeds with a binder and other inert materials to facilitate mechanical planting of seeds and protect the seeds once they are planted.

In this embodiment the method is preferably used to enhance or inhibit seed metabolic activity to influence seed germination and derived plant growth and development under a range of environments that include the presence and absence of abiotic and/or biotic stress. Further, in this embodiment, the method of incorporating the plant bio-regulators into seed coating systems is preferably used to augment incorporation of the plant bio-regulators into seed priming systems.

In another embodiment a method of seed treatment is encapsulation of the seed with a material forming the capsule surrounding the seed. Examples of encapsulation systems include interfacial polymerization, in-situ polymerization, matrix polymerization and the like. For example, in matrix polymerization a core material is imbedded in a polymeric matrix during formation of the particles. A simple method of this type is spray-drying, in which the particle is formed by evaporation of the solvent from the matrix material. However, the solidification of the matrix also can be caused by a chemical change. In Interfacial polymerization, the two reactants in a polycondensation meet at an interface and react rapidly. In yet another embodiment, in situ polymerization the direct polymerization of a single monomer is carried out on the particle surface.

Both the foregoing general description and the following detailed description are exemplary and explanatory only and are not necessarily restrictive of the invention as claimed. The accompanying drawings, which are incorporated in and constitute a part of the specification, illustrate embodiments of the invention and with the general description, explain the principles of the invention.

DETAILED DESCRIPTION

The present invention includes compositions, systems, and processes for enhancing or modifying expression of particular gene products to produce desirable improvement in specific plant properties related to internal and external plant characteristics and overall agricultural output. The methods and processes are useful in seed encapsulation, coating, and soaking; plant spraying and rhizosphere drenching. Further objects of the inventions will be evident from the following description, wherein, parts and percentages are by weight unless otherwise specified.

A benefit of the present invention can be obtained by applying the described compositions in bio-regulatory amounts to the sexual reproductive parts and vegetative parts of plants, which can include but are not limited to seeds, bulbs, roots, seedlings, growing plants, slips, and cuttings (plants include trees). Practically, this can be done via soaking plant parts in a solution containing the active bio-regulator composition; applying the bio-regulator solution during the seed priming process; applying the bio-regulator to seeds with a binder and other inert materials; dusting the seeds with a powder containing the bio-regulator composition; spraying the seed in furrow with a bio-regulator solution or dusting the seed with a powder formulation containing the bio-regulator prior to covering the seed; encapsulation; spraying the cotyledon before transplanting or while in the furrow; spraying the vegetative parts of the plant at various stages of plant development; dusting the cotyledons before transplanting or while in the furrow; dusting various parts of the plant at various stages of plant development; irrigating the roots or plants with solvent mixed with bio-regulator compositions before transplanting or while in the furrow; and through other methods of application.

Figure 1A:
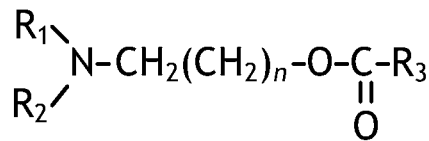
FIG. 1a shows a general chemical structure of a compound according to at least one embodiment of the present invention.
Figure 1B:
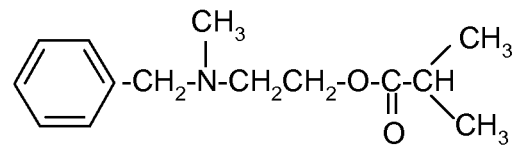
FIG. 1b shows a chemical structure of a compound according to at least one embodiment of the present invention.
Figure 1C:
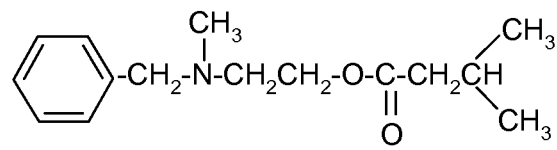
FIG. 1c shows a chemical structure of a compound according to at least one embodiment of the present invention.
Figure 1D:
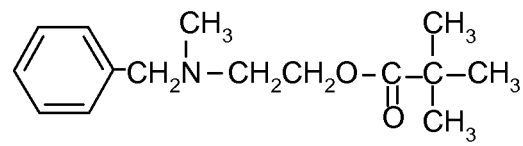
FIG. 1d shows a chemical structure of a compound according to at least one embodiment of the present invention.
Figure 1E:
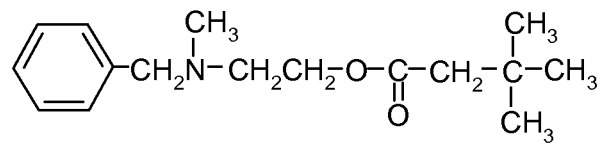
FIG. 1e shows a chemical structure of a compound according to at least one embodiment of the present invention.
Figure 1F:
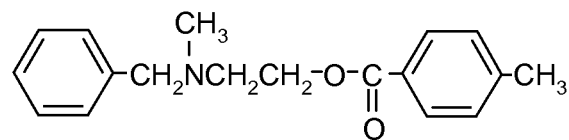
FIG. 1f shows a chemical structure of a compound according to at least one embodiment of the present invention.
Figure 1G:
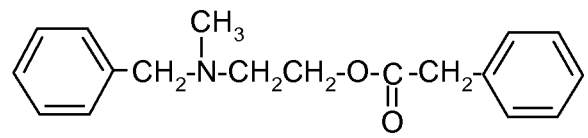
FIG. 1g shows a chemical structure of a compound according to at least one embodiment of the present invention.
Figure 1H:
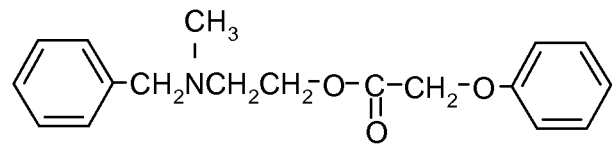
FIG. 1h shows a chemical structure of a compound according to at least one embodiment of the present invention.
Figure 1I:
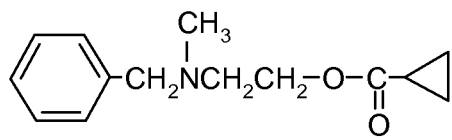
FIG. 1i shows a chemical structure of a compound according to at least one embodiment of the present invention.
Figure 1J:
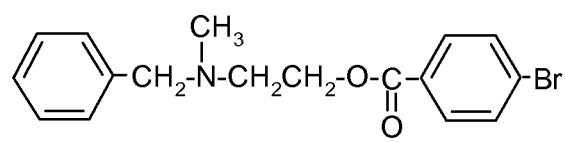
FIG. 1j shows a chemical structure of a compound according to at least one embodiment of the present invention.
Figure 1K:
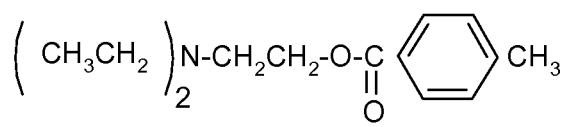
FIG. 1k shows a chemical structure of a compound according to at least one embodiment of the present invention.
Figure 1L:
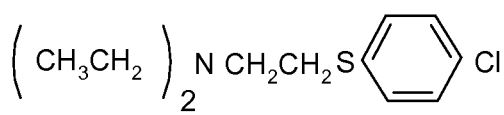
FIG. 1l shows a chemical structure of a compound according to at least one embodiment of the present invention.
Figure 1M:
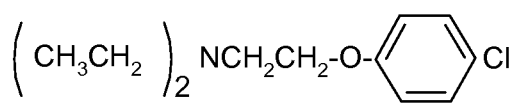
FIG. 1m shows a chemical structure of a compound according to at least one embodiment of the present invention.
Figure 1N:
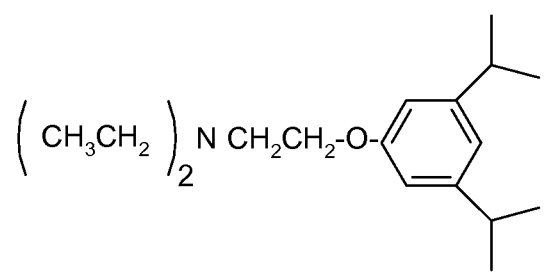
FIG. 1n shows a chemical structure of a compound according to at least one embodiment of the present invention.
Figure 1O:
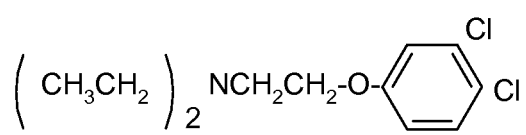
FIG. 1o shows a chemical structure of a compound according to at least one embodiment of the present invention.
Figure 2A:
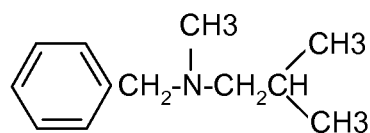
FIG. 2a shows a chemical structure of a compound according to at least one embodiment of the present invention.
Figure 2B:
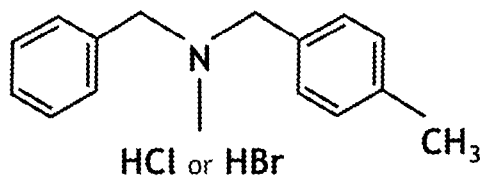
FIG. 2b shows a chemical structure of a compound according to at least one embodiment of the present invention.
Figure 2C:
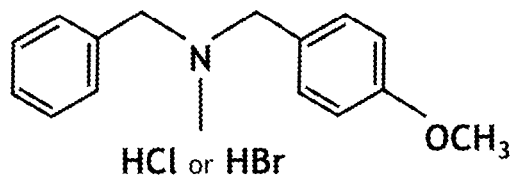
FIG. 2c shows a chemical structure of a compound according to at least one embodiment of the present invention.
Figure 2D:
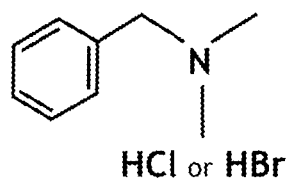
FIG. 2d shows a chemical structure of a compound according to at least one embodiment of the present invention.
Figure 2E:
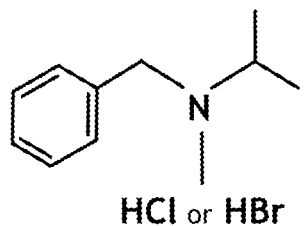
FIG. 2e shows a chemical structure of a compound according to at least one embodiment of the present invention.
Figure 2F:
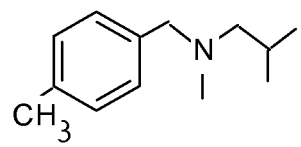
FIG. 2f shows a chemical structure of a compound according to at least one embodiment of the present invention.

Bio-regulator solutions are prepared by selecting compositions from the following groups of classes of compositions:

A. Ester Compounds:

Referring to FIGS. 1a-1o, chemical compounds are shown that may be regarded as "Ester Compounds." A person skilled in the art may appreciate that Ester Compounds as represented by FIGS. 1a-1o may encompass other compounds not specifically listed.

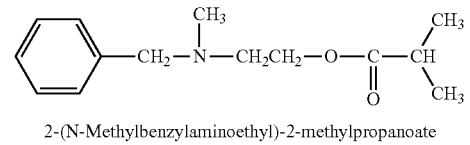

2-(N-Methylbenzylaminoethyl)-2-methylpropanoate
(BMBE)

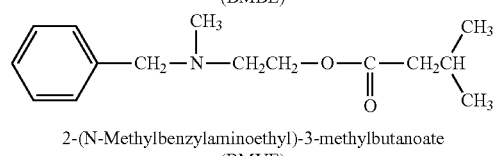

2-(N-Methylbenzylaminoethyl)-3-methylbutanoate
(BMVE)

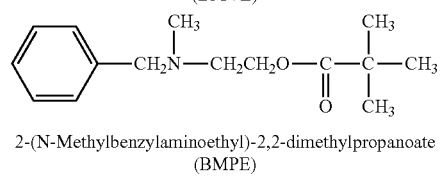

2-(N-Methylbenzylaminoethyl)-2,2-dimethylpropanoate
(BMPE)

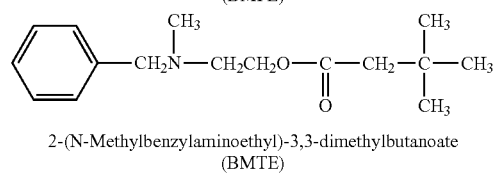

2-(N-Methylbenzylaminoethyl)-3,3-dimethylbutanoate
(BMTE)

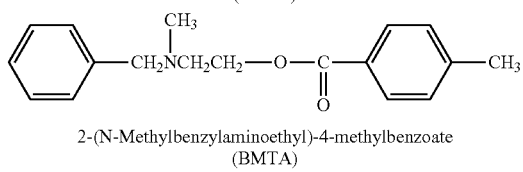

2-(N-Methylbenzylaminoethyl)-4-methylbenzoate
(BMTA)

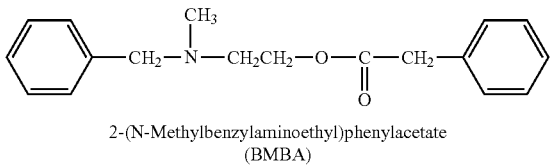

2-(N-Methylbenzylaminoethyl)phenylacetate
(BMBA)

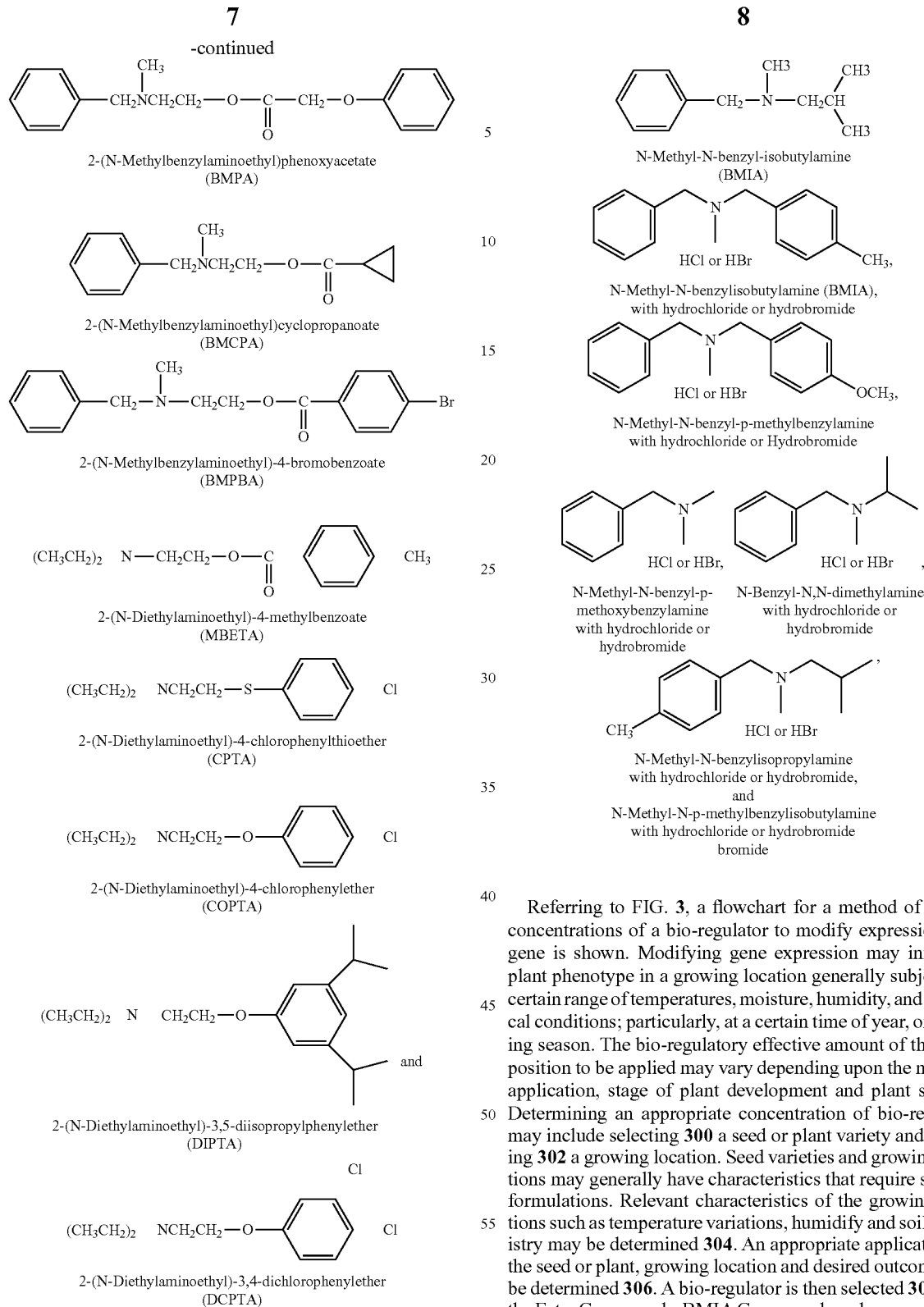

B. BMIA Compounds

Referring to FIGS. 2a-2f, chemical compounds are shown that may be regarded as "BMIA Compounds." A person skilled in the art may appreciate that BMIA Compounds as represented by FIGS. 2a-2f may encompass other compounds not specifically listed.

Figure 3:
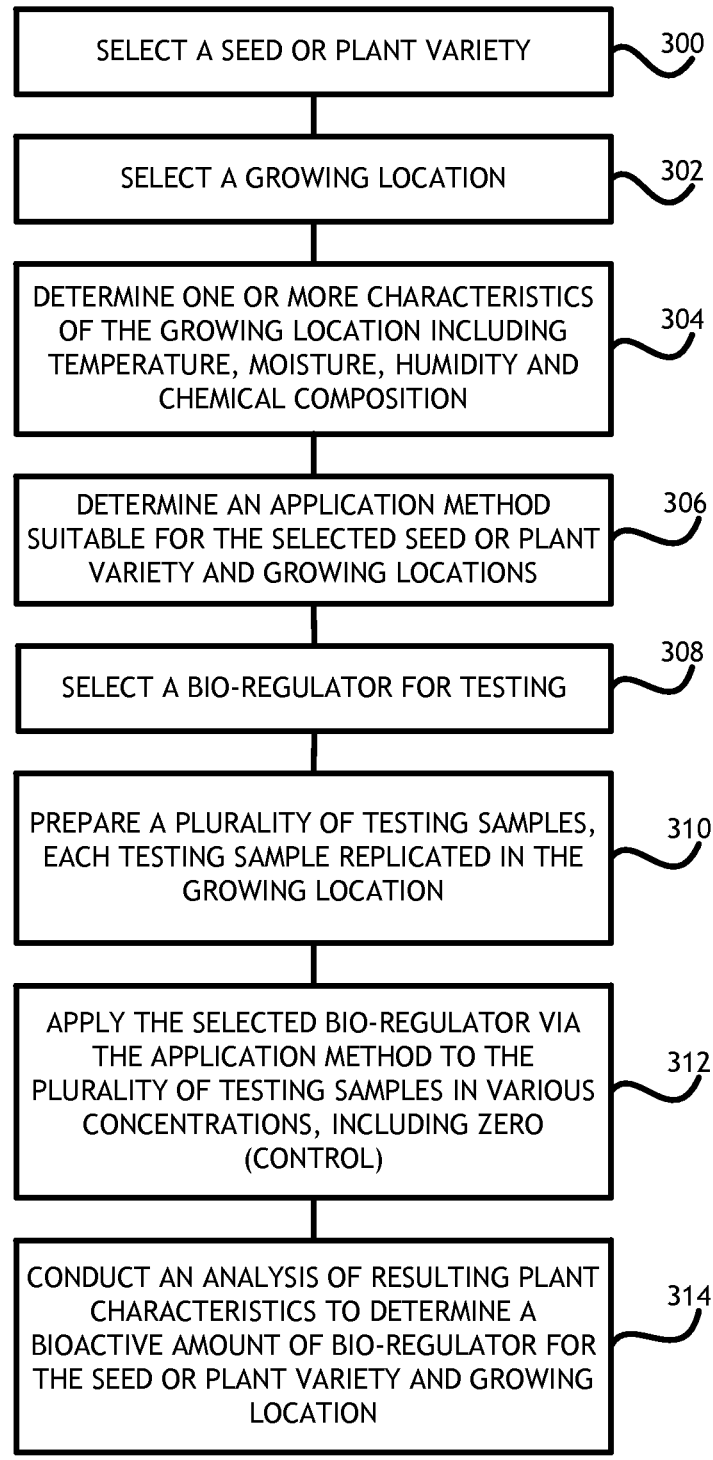
FIG. 3 shows a flowchart for a method of testing concentrations of a bio-regulator to modify a gene expression.

Referring to FIG. 3, a flowchart for a method of testing concentrations of a bio-regulator to modify expression of a gene is shown. Modifying gene expression may influence plant phenotype in a growing location generally subject to a certain range of temperatures, moisture, humidity, and chemical conditions; particularly, at a certain time of year, or growing season. The bio-regulatory effective amount of the composition to be applied may vary depending upon the mode of application, stage of plant development and plant species. Determining an appropriate concentration of bio-regulator may include selecting 300 a seed or plant variety and selecting 302 a growing location. Seed varieties and growing locations may generally have characteristics that require specific formulations. Relevant characteristics of the growing locations such as temperature variations, humidify and soil chemistry may be determined 304. An appropriate application for the seed or plant, growing location and desired outcome may be determined 306. A bio-regulator is then selected 308 from the Ester Compounds, BMIA Compounds and corresponding Salt Compounds described herein. A plurality of testing samples is prepared 310. Each testing sample may replicate at least some characteristics of the growing location. Where testing is concerned with seed treating, the selected bio-regulator is applied 312 via soaking, coating, priming or other seed treating methods. Where testing is concerned with developing plant treating, the selected bio-regulator is applied 312 via spraying, dusting or other such methods. In either case, testing samples may be treated with the selected bio-regulator at varying concentrations to determine a minimum and maximum bio-regulatory effective concentration. After an appropriate growth duration to assess the effectiveness of the bio-regulator, an analysis is conducted 314 to determine if the selected bio-regulator was effective and what concentrations or amounts produced the desired results.

Figure 4:
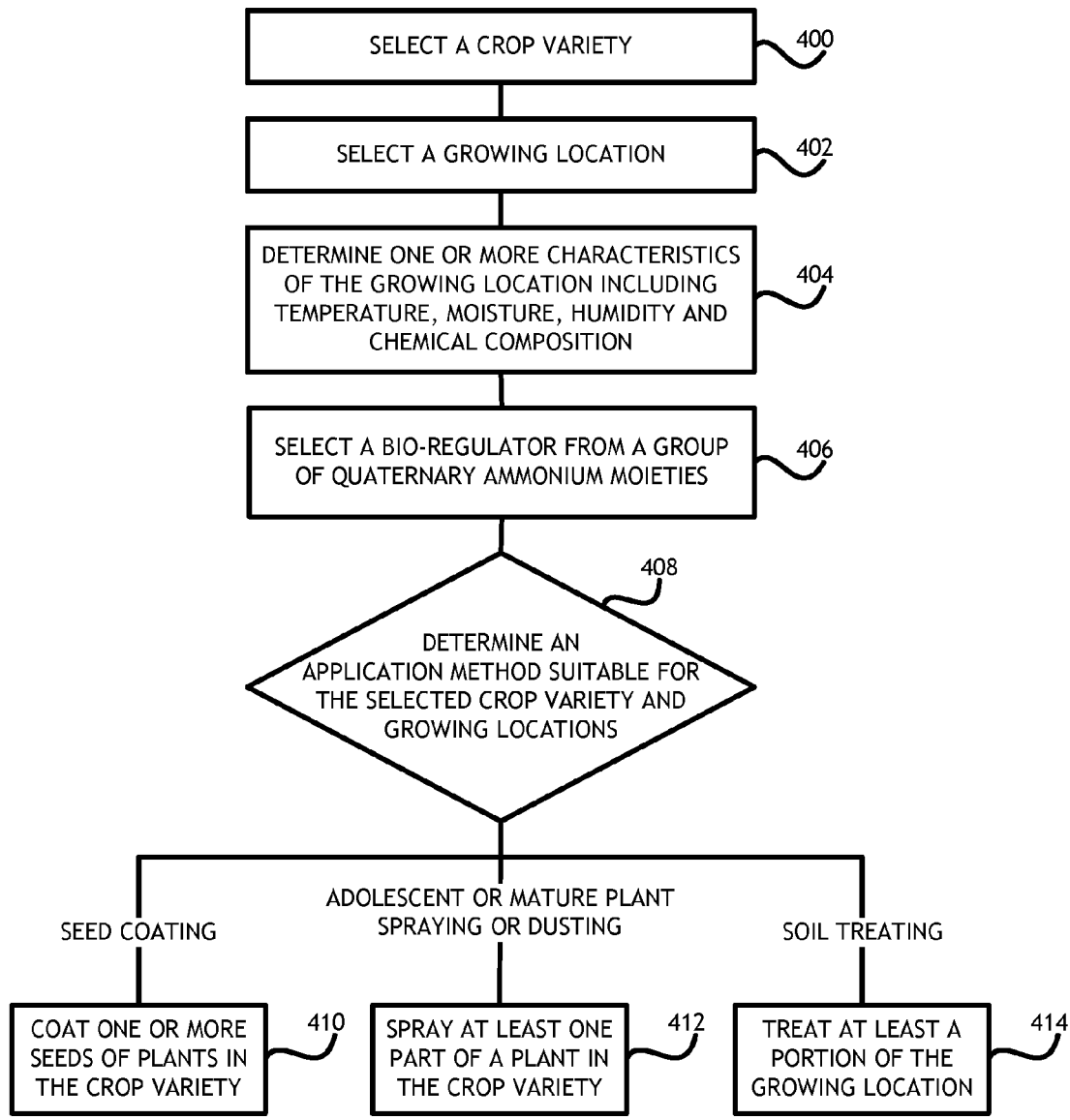
FIG. 4 shows a flowchart for a method of treating a crop to modify a gene expression.

Referring to FIG. 4, a flowchart for a method of treating a crop to modify a gene expression is shown. Modifying one or more gene expressions may generally enhance crop productivity. First, a crop is selected 400 or identified; then the growing location is selected 402 or identified. Characteristics of the growing location such as temperature, moisture, humidity and soil chemistry are determined 404. Based on those characteristics, a bio-regulator is selected 406 to enhance crop productivity at the particular location. An application method is determined 408 based on the crop, growing location and desired result. Based on the determined application method, crop seeds are coated 410, crop plants are sprayed or dusted 412, or growing location soil is treated 414.

Figure 5:
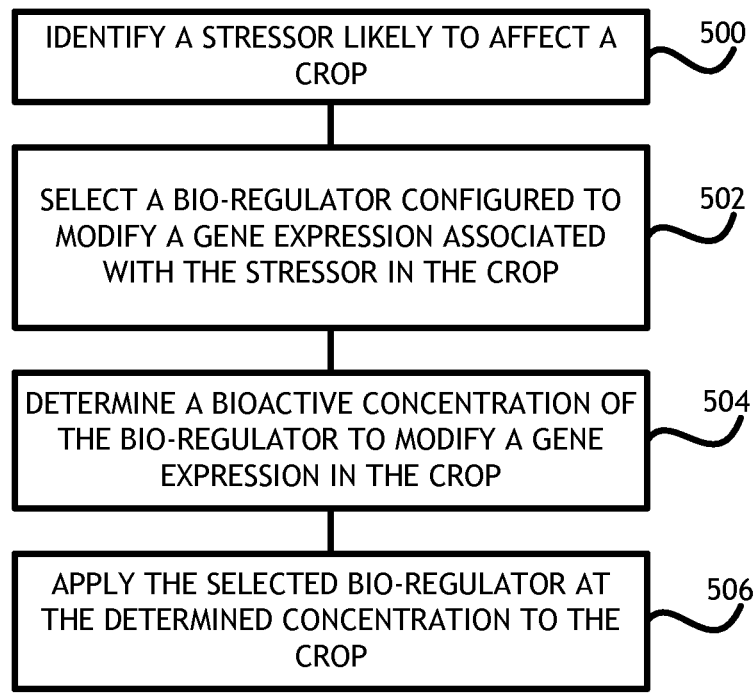
FIG. 5 shows a flowchart for a method of testing concentrations of a bio-regulator to modify a gene expression based on a stressor.

Referring to FIG. 5, a flowchart for a method of testing concentrations of a bio-regulator to modify a gene expression based on a stressor is shown. Where a crop is undergoing or expected to undergo a specific stressor, a bio-regulator specific to the crop and the stressor may be used to enhance the robustness of the crop to the particular stressor. Specific stressors such as temperature variations, moisture, humidity or soil chemistry are identified 500. A previously tested bio-regulator is selected 502 based on the stressor to modify one or more gene expressions. An appropriate concentration of bio-regulator is determined 504 based on previous testing and the concentration of bio-regulator is applied 506 to the crop, either as seeds or growing plants.

In one exemplary test, microarray and illumina analyses were performed on monocot and dicot plant tissues treated with bio-regulator compounds to see what genes were expressed as a result. Based on the types of genes expressed, it may be determined how plants treated with a particular dose of a particular bio-regulator might perform in certain environmental conditions. For example bio-regulator compound treatments on soybean, corn and *Arabidopsis* leaf tissue may result in expression of genes associated with heat, drought, and salt tolerance in plant tissue.

In another exemplary test, a large factorial screening test was performed where seeds and/or plants of a range of plant species were treated with a dose range of each of a number of bio-regulators according to embodiments of the present invention and then grown out in a growth chamber set to a certain environmental stress condition or in a potting medium incorporating a stress component (i.e. NaCl). Phenotype assessments (root and shoot dry weights, root-shoot ratios, plant height, flowering characteristic ratings, etc. . . . ) may be done during and at the end of the grow-out. Such screening test may be the basis for selecting a bio-regulator compound and dose that result in optimum performance in that particular environment. Similar types of screening at a different grow-out scale may be performed to assessing performance of plants treated with a bio-regulator and then exposed to pathogenic microbe/insect pressure.

Application of the bio-regulator compounds to seeds prior to exposure of the seeds and resultant plants to abiotic and/or biotic stress and prior to resultant plants achieving growth stages in which yield factors such as seed size and seed number are set, is preferred. Use of an active bio-regulator above certain threshold concentrations may inhibit growth of the resultant plants and even exhibit phytotoxic effects on the resultant plants, which in some circumstances may also be a desired result.

In at least one embodiment of the present invention, appropriate wetting agents and penetrating adjuvants are included in the composition. Such agents may include but are not limited to: Triton X-100 (polyoxythylene glycol p-isooctylphenylether made by J. T. Baker), ORTHO X-77 (a mixture of fatty acids, fatty alcohols and isopropanol made by Chevron Chemical Company), Sweep 4F (chlorothalonil from Diamond Shamrock Company), Kinetic® (a proprietary blend of polyalkyleneoxide modified polydimethylsiloxane and (nonionic surfactant) polyoxypropylene block copolymers made by Helena Chemical Company). These or similar agents may be added to the aqueous solution to aid in seed treatment. Appropriate penetrating agents can also be added to the solution to increase penetration of the bioregulator compound. These penetrating agents could include, but are not limited to: B-cyclodextrin (B-(heptamer)-cyclodextrin made by Takeda Chemical Industries, Ltd.) or Tween (polyoxyethlene (20) sorbitan monooleate, available from E. Merck, Darmstadt, Germany).

C. Methods for Seed Application

1. Seed Soaking

In a preferred embodiment of the present invention, the bio-regulator compositions according to this invention are applied to seeds in the amount of about 0.001 mg to 0.5 mg of active bio-regulator ingredient per seed via bio-regulator solution. Bio-regulator solution is made by dissolving the composition to be used into a solution (solvent—preferably water, surfactants, and other appropriate wetting agents and penetrating adjuvants) at a concentration of preferably 0.05 to 200 ppm. When using soaking as the method of bio-regulator solution application, seeds should be preferably soaked for one quarter hour to 24 hours. Other methods of application to seeds such as encapsulation, gel-coating, spraying, coating, dusting, seed priming and the like with the bio-regulator compositions can be accomplished according to conventional methods, and are encompassed and contemplated by this invention In other embodiments, the bio-regulatory effective amount of the composition to be applied may vary depending upon the seed species and cultivar and the desired overall effect. Generally, to achieve growth enhancement, treatment to seeds prior to the stages of plant development is preferred. The degree of penetration of the bio-regulator composition into the seed will be a factor in the overall growth enhancement achieved, and is dependent in part upon whether or not one or more penetrating agents are used.

2. Seed Coating

In another embodiment of the invention, the process of seed coating is employed. Seed coating involves application of certain active ingredients, including but not limited to fungicides, insecticides, plant growth promoting compounds, beneficial microbes, to seeds with a binder and other inert materials to facilitate mechanical planting of seeds and protect the seeds once they are planted.

The process of seed coating generally is well-known in the art. It is often achieved as pharmaceutical coating is achieved (i.e. through applying a mist, then an inert powder, and finally a binder). When the bio-regulator solutions or bio-regulator compositions are incorporated into a seed coating process, the desired plant growth enhancement can be achieved.

Application of bio-regulator solution or bio-regulator compositions can be achieved when the seeds are misted with solution (preferably water) by adding the bio-regulator solution to the applied mist in similar concentrations as compared to soaking. Application can also be achieved by applying a mixture of powderized bio-regulator compositions and inert powder after the misting stage (crystalline, or inert particulate materials impregnated with bio-regulator). Again, the concentrations used when incorporating a powderized form of bio-regulator composition will be similar to the concentrations used when soaking (i.e. 0.05 to 200 ppm or 0.00002 mg to 0.5 mg per seed).

In another embodiment, bio-regulator solutions can also be used with fungicides and insecticides. The bio-regulator solution can be tank-mixed with most seed protection products provided such products are miscible in water and labeled for slurry application directly on seed. Alternatively, the bio-regulator may not need to be mixed and miscible in water if applied by appropriate spray systems. Compatibility can be checked by mixing a small amount of each product together to confirm suitability of slurry application prior to application.

In another embodiment, the bio-regulator solutions can also be used with biological products. They can be sequentially or simultaneously applied with most biological products when mixed in separate mix tanks or applied by direct tank mixing the bio-regulator solution in the same tank with biological products such as legume inoculants, beneficial fungi, and other live microorganisms.

In this embodiment the method is preferably used to enhance or inhibit seed metabolic activity that is made amenable to bio-regulator compound activity as a function of the metabolic status achieved and maintained during or following the seed priming process to influence seed germination and derived plant growth and development under a range of environments that include the presence and absence of abiotic and/or biotic stress.

D. Method for Application During Stages of Plant Development

Although seed treatment prior to the stage of plant development is preferred, in other embodiments of the present invention, treatment may occur at any stage of plant development. When application is made to the seedling, or at the cotyledon, true leaf, two-leaf or four-leaf stages, etc., the preferred treatment includes about 0.0001 mg to 0.3 mg bio-regulator ingredient per plant. This can be accomplished by using a treatment rate of about 0.1 to about 200 ppm and preferably from about 1 to about 120 ppm. Application according to this method preferably follows the emergence of the first true leaf and thinning, if thinning is necessary. Then, when the vegetative plant begins to develop, the bio-regulator solution may be sprayed, dusted, or otherwise applied to the plant at a particular stage of development or at multiple stages of the plant's development. Application during stages of plant development is in embodiments directed toward influencing efficacious production of particular metabolic end products, plant yield, abiotic and/or biotic stress tolerance or pest resistance, or accelerating and enhancing herbicide activity in a plant burndown application.

Generally, to achieve increased herbicide phytotoxicity and plant kill rate (i.e. burndown), spray treatment with the bio-regulator included at a desired concentration into the herbicide spray composition is the preferred method. In at least one exemplary embodiment, plants treated with a combination of a herbicide and a bio-regulator according to one embodiment of the present invention were killed 3 to 5 days faster as compared to herbicide alone. A person skilled in the art may appreciate that use bio-regulation to increase herbicide phytotoxicity may reduce the overall need for herbicide, and thereby reduce the environmental and economic impact of such herbicides.

E. Method for Application to Plants That Asexually Propagate

In another embodiment of the present invention, methods for application to asexually propagating plants are considered. There are a variety of plants capable of asexual propagation. Cuttings are the parts of plants severed from the parent to initiate the propagation. Once the cuttings are formed, they may be rooted or grafted using a rooting medium. Rooting is the preferred time for treatment with the bio-regulatory solution. However, the bio-regulatory solution can also be applied after rooting and during transplantation, or during subsequent irrigation. Transplanting is done by means generally known to those skilled in the art. The cuttings and graftings are then irrigated and given the requisite amount of sunlight for maximum growth.

The bio-regulator solutions used to treat the cuttings are formed from the groups of compositions from the groups mentioned above (i.e. BMTA, BMVE, and BMIA), water, and appropriate wetting agents and penetrating adjuvants.

1. Hypothesis and Theory

Without any intention of limiting the scope of the invention, it is theorized that the bio-regulatory and stimulatory compositions used in the method of this invention play a role in the physiological development of the plant by conferring beneficial enhancements from the seed stage and throughout a plant's full life cycle. This theory is formulated after observing that test plants are found to achieve various beneficial characteristics, which increase the plant biomass, while untreated, control plants, which were grown under similar conditions as the test plants, did not exhibit these same growth enhancements. This theory is also furthered by the chemical compositions and formulations used in this method, and the known and unknown effects these compositions and formulations have on plants at the physiological and molecular level. It should also be noted that all compositions are not active for all species but each of the plants tested did result in some form of enhancement via a combination of the bio-regulatory compositions.

Furthermore, similar biological mechanisms may be involved in activating gene expression in a manner that renders particular plants more susceptible to a burndown herbicide application when the bio-regulator compounds are included in the herbicide mix and applied to the plants in appropriate concentrations. For example, a bi-regulatory active concentration of a composition according to the present invention may modify the expression of a gene or genes that may be detrimental to the growth of an undesirable plant in a given environment.

F. Genetic Expression Studies

Modifications to gene expression in seeds and plants can occur when seeds and plants are exposed to particular ecological and chemical factors, including abiotic and/or biotic stresses, plant growth promoting compounds, systemic acquired resistance (SAR) promoting compounds, and various pesticide compounds, including fungicides, insecticides and herbicides. Modifications to gene expression in seeds and plant can vary according to the ecological and/or chemical factor to which the seed or plant is exposed. For example, when seeds and plant experience abiotic or biotic stresses, mRNAs transcribed from a complement of genes activated as part of a stress response produce proteins that aid in protecting the against the particular abiotic or biotic stress experienced by the seed or plant; if the stress is high temperature, the proteins expressed serve in protecting against injury from high temperatures. Similarly, seeds and plant express certain gene protein products in response to SAR promoting compounds that play roles in protecting against pathogens. Further, seeds and plant express gene protein products in response to exposure to plant growth promoting compounds that play roles in acceleration of growth and development and/or increased growth in the presence or absence of abiotic and/or biotic stresses. Proteins expressed in seeds and plant in response to exposure to certain pesticide compounds may or may not augment the function of the particular pesticide compounds. Plant phenotypes resulting from the interaction of seeds and plants with such ecological and chemical factors is a function of how gene expression is influenced by such factors.

Given the enhanced phenotypes produced in the absence and presence of abiotic and biotic stresses as a function of treatment of seeds and plants with the bio-regulators, one object of the studies of embodiments of the present invention set forth herein was to characterize gene expression in seeds and plant treated with different bio-regulator compound compositions according to the present invention. Accordingly, a series of studies were conducted of embodiments of the present invention in order to illustrate the effect compositions of a model bio-regulator, BMVE, have on gene expression in monocotyledonous and dicotyledonous plant species. The studies were conducted on the dicotyledonous plant species, *Arabidopsis* and soybean and the monocotyledonous plant species, maize.

Gene expression analyses involved extracting mRNA from leaves of plants grown in a greenhouse under non-stress conditions approximately 15 hours following a foliar spray application of 3 ppm BMVE solution, and extracting mRNA from leaves of plants grown in a greenhouse under non-stress conditions and not treated with the BMVE solution (control plants). The extracted mRNA products were then analyzed by microarray analysis in the case of *Arabidopsis* and maize, and microarray and Illumina analyses in the case of soybean. The analyses identified which genes were either "up-regulated" or "down-regulated" by the BMVE treatment based on comparing quantities of particular gene products extracted from the plants treated with BMVE to the corresponding gene products extracted from the baseline control plants. Up-regulated genes were increased due to the BMVE treatment, and down-regulated genes were decreased due to the BMVE treatment. Once up-regulated and down-regulated genes were identified in each of the plant species by microarray analysis, the genes were compared to genes in known gene databases for each species to determine the function for each gene.

In one study of an embodiment of the present invention, the gene expression profile of *Arabidopsis* plants treated with BMVE was compared to the *Arabidopsis* eFP Browser database gene expression profiles for *Arabidopsis* plants exposed to certain chemical applications, hormone applications, biotic stresses, and abiotic stresses. The microarray and comparison results indicated that genes involved in protecting plants from abiotic and biotic stresses and facilitating general growth and development were influenced by the BMVE treatment. There were 127 genes up-regulated by the BMVE treatment, including pathogen defense response genes, JA-response genes, Lipoxygenases, chitin-responsive proteins, dehydrin proteins, WRKY transcription factors that are particularly involved in plant persistence in diverse abiotic and biotic stress environments, and root development genes. The plants treated with BMVE generally expressed 54 down-regulated genes including auxin-responsive proteins and transcription factors.

In another study of an embodiment of the present invention, soybean plant microarray and Illumina gene expression analyses were also studied in a similar fashion as compared to the *Arabidopsis* study and the study indicated that genes involved in protecting plants from abiotic and biotic stresses and facilitating general growth and development were influenced by treatment with BMVE. The result of the soybean plant microarray showed that there were 645 genes affected by the BMVE treatment. Up-regulated genes included pathogenesis-related and pathogen defense genes. Down-regulated genes included proteinase inhibitors (PR-6) and WKRY transcription factors.

In another study of an embodiment of the present invention, maize plants were treated with BMVE. The results generally indicated that there were a smaller number of genes affected in maize than in the soybean microarray analysis. The particular genes influenced by treatment with BMVE were not identified due to limitations of the maize genome database.

In these studies, plants were used, instead of the embryonic axis of seeds, for example, because of the practicality of extracting mRNA from large quantities of leaf tissue as contrasted to smaller quantities of seed embryo tissue. Outside of genes associated with particular plant developmental stages, it is expected that, within species and cultivar, influences of the bio-regulator compound, BMVE, on genes involved in protecting plants from abiotic and biotic stresses and facilitating general growth would be similar at the seed embryo through mature plant stages of development. Further, in these studies, compound BMVE was investigated as a model bio-regulator compound in order to help define mechanisms associated with the improved phenotypes resulting from bio-regulator treatment of seeds and plants prior to and during growth in the presence and absence of abiotic and biotic stresses. Given phenotypes within a plant species and cultivar vary in either a non-stress or abiotic and biotic stress environment according to the bio-regulator compound used in treatment, it is expected that gene expression profiles within a plant species and cultivar will vary in accordance with the bio-regulator compound used in treatment.

A person skilled in the art may appreciate that the bio-regulatory effects produced by compositions according to embodiments of the present invention may not be limited to plant organisms. Gene expression in fungi and algae may also be subject to bio-regulation. In at least one embodiment of the present invention, microorganisms exposed to treatment with a bio-regulator according to embodiments of the present invention demonstrated modified gene expression. Furthermore, such modified gene expression persisted generationally even when no bio-regulator was present. In one example, such modified gene expression persisted for two generations.

Bio-regulation of microorganisms may include modifying gene expression of beneficial microorganisms to enhance their growth and vitality. Conversely, bio-regulation of microorganisms may include modifying gene expression of harmful microorganisms to suppress them or make them more susceptible to other biological or chemical agents.

G. EXAMPLES

Studies of embodiments of the present invention encompassing various types of plants and seeds with various concentrations of applied bio-regulatory compositions have further illustrated the effectiveness of the bio-regulator compositions, solutions, and the application methods and procedures contained herein. In these embodiments, test plants that have been treated with the bio-regulatory compositions were compared to control plants. Each of the groups of plants is grown under similar environmental conditions. After different lengths of time, test plants are compared to control plants, considering both internal and external physical characteristics. These studies took place in various geographic locations including Malaysia, California, Nebraska, Kansas, and Oklahoma.

1. General Procedure for Seed Soaking Treatment for Growth Enhancement of Agricultural Crops and General Flora:

In this preferred embodiment of the present invention, seeds are soaked in prepared bio-regulator solutions for a period of one half to four hours depending on the absorption property of the seeds. The bio-regulator solutions are prepared in concentrations ranging from 0.1 ppm to 100 ppm using compositions selected from the BMIA Compounds or Ester Compounds. Because size and absorption characteristics of seeds vary, the soak time for each seed will also vary. For example, a particular cotton seed may take at least four hours for good uptake of bio-regulator into the seed. At the end of the soaking period the solution is drained and while still wet, the seeds are planted into starter potting soil or directly into soil. Rather than directly planting the seeds, they may be dried for planting at a later point. After germination seedlings are transplanted to larger pots or to open soil.

a. Specific Examples

Example I

General Procedure for Seed Soaking Treatment of Agricultural Crops using Rice Seeds In another preferred embodiment of the present invention, seeds are soaked in prepared bio-regulator solutions for a period of three hours. Rice seeds were selected from 'M-202' medium-grain rice (*Oryza sativa* L.), (Reg. no 72) PI494105 type grains; this selection was meant to represent a typical California rice seed, and was not meant to be limiting. The bio-regulator solutions are prepared using 5 ppm BMTA solution with 0.05% v/v Kinetic® made by Helena Chemical Company. The solution was drained and the seeds planted in starter plastic containers with potting soil. After germination and having grown to 4 inches in height, the plants were transplanted into 6 inch diameter plastic containers. Two sets of three pots each were set up for this study; one set for the test group and one set for the control group.

Both the control and test studies were irrigated with 1500 ppm NaCl solution from time of planting until the study was completed. The purpose of the NaCl irrigation was to determine the effect of the bio-regulator treatment in regards to salt tolerances.

It was observed that the BMTA treated rice plant showed enhanced growth from the time of planting, through completion of the study. The plant had observable increased biomass, tillering, and foliage.

In this embodiment, the effect of the bio-regulator solution on rice seed (Tables 1-A and 1-B) was studied. Those skilled in the art will recognize that the effects, results and outcomes may be achievable following a similar procedure for other types of cereal grains and monocot plants.

This example is summarized in Table 1-A below, where Set 1 is the control, and Set 2 is the test group. The results are summarized in Table 1-B:

TABLE 1-A

| Set # | Treatment | Ppm | Soak Time | Irrigation | Surfactant |
|---|---|---|---|---|---|
| Set 1 | Tap water | 0 | 3 hours | NaCl soln. | Kinetic ® |
| Set 2 | BMTA soln. | 5 | 3 hours | NaCl soln. | Kinetic ® |

TABLE 1-B

| Results | Biomass | Height | Tillering |
|---|---|---|---|
| Set 1 | Average | Average | Average |
| Set 2 | ~3 x Set 1 | Same | ~3 x Set 1 |

Example II

In this preferred embodiment of the present invention, seeds are soaked in prepared bio-regulator solutions for a period of 24 hours. Rice seeds were selected from the same 'M-202' type grains as in the previous study. The bio-regulator solutions were prepared using 5 ppm BMPA solution. The solution was drained and seeds planted in starter plastic containers filled with potting soil. After germination and plant growth reaching height of four inches, rice seedlings were transplanted from their greenhouse containers to six-inch diameter plastic containers and placed outdoor. Again, two sets of three pots for the control and test group were used.

It was observed that the BMPA treated rice plant showed enhanced growth from the time of planting, through completion of the study. The plant had observable increased biomass, tillering, and foliage. This method and bio-regulator solution produced greater growth enhancement than the previous example's method and procedure.

These studies were also carried out using an increased amount of BMPA. The amount was increased from 1 ppm to 5 ppm, and the results of the study were similar to the results outlined in the paragraph above.

The study of this embodiment is summarized in Tables 2-A and 2-B below, where Set 1 is the control, and Set 2 is the test group. The results are summarized in Tables 2-C and 2-D:

TABLE 2-A

| Set # | Treatment | Ppm | Soak Time | Irrigation | Surfactant |
|---|---|---|---|---|---|
| Set 1 | Water | 0 | 24 hrs | Tap water | Kinetic ® |
| Set 2 | BMPA | 5 | 24 hrs | Tap water | Kinetic ® |

TABLE 2-B

| Set # | Treatment | Ppm | Soak Time | Irrigation | Surfactant |
|---|---|---|---|---|---|
| Set 1 | Water | 0 | 24 hrs | Tap water | Kinetic ® |
| Set 2 | BMPA | 1 | 24 hrs | Tap water | Kinetic ® |

TABLE 2-C

| Results | Biomass | Height | Tillering |
|---|---|---|---|
| Set 1 | Average | Average | Average |
| Set 2 | ~4 x Set 1 | ~1.2 x Set 1 | ~4 x Set 1 |

TABLE 2-D

| Results | Biomass | Height | Tillering |
|---|---|---|---|
| Set 1 | Average | Average | Average |
| Set 2 | ~4 x Set 1 | ~1.2 x Set 1 | ~4 x Set 1 |

Example III

General Procedure for Treatment of Floral Plant Cuttings in General and Geranium Slips in Particular In this preferred embodiment of the present invention, according to common geranium cutting means, geraniums were slipped into 18 slips of similar length. In this example the slips had no flower buds. The slips were separated into four different sets: three slips each in three of the sets, and then nine slips in the final set. The slips are then treated with bio-regulator solutions formed from compositions from the different groups and water. In the first set, the slips were treated with BMVE solution; in the second set, the slips were treated with BMTA solution; in the third set, the slips were treated with BMIA in bromide solution; and, in the fourth set, the nine slips were treated with water.

The treatment with bio-regulator solution preferably occurs in the initial planting of the geranium slips, but can also occur at any time from the forming of the geranium slips up to and including the transplanting of the slips. The treatment can occur after transplanting, but this is not the preferred method.

Transplanting can be done by means generally known to those skilled in the art. In this example the slips were transplanted into 6-inch diameter pots and filled with potting soil. Each of the pots were identified as belonging to the first, second, third, or fourth set. Each pot, after transplantation, was thoroughly irrigated with water. Each set of pots were placed outside for maximum sunlight, for eight hours per day.

It was observed that the treated geranium slips generally showed enhanced growth from the time of transplanting, through completion of the study. The slips had observable increased vigor even when compared with slips that had a greater number of leaves.

In this embodiment, the effect of bio-regulator solutions on geranium slips was studied; however, it is anticipated that similar effects, results, and outcomes will be achievable following a similar procedure as outlined above for other types of plants that reproduce through vegetative propagation.

The study associated with this embodiment is summarized in Table 3-A below, where Set 1 is the control group and Set 2 is the test group. The results are summarized in Table 3-B. Included for convenience is Table 3-C, which summarizes the total test heights to control heights ratios. The ratios for Table 3-C are calculated by totaling the heights grown by each slip in each set and comparing it to the control counterpart that was grown in similar environmental conditions, without the treatment of the bio-regulator solutions. The total heights grown by the test slips are also compared to the control slips by a percentage of the overall height of the control slips.

TABLE 3-A

| Set # | Number of Slips | Treatment | Depth Planted (in.) |
|---|---|---|---|
| Set 1 | 3 | BMVE | 2½ |
| Set 2 | 3 | BMTA | 2½ |
| Set 3 | 3 | BMIA | 2½ |
| Set 4 | 9 | Water | 2½ |

TABLE 3-B

| Day | Set # | PGS Treatment | Dosage (ppm) | Slip 1 Ht. (in.) | Slip 2 Ht. (in.) | Slip 3 Ht. (in.) |
|---|---|---|---|---|---|---|
| 11 | 1 | BMVE | 5 | 2¼ | 2⅞ | 3⅜ |
|  | 4 | Water |  | 2⅛ | 2⅜ | 2¼ |
|  | 2 | BMTA | 5 | 2¾ | 2¾ | 3⅛ |

TABLE 3-B-continued

| Day | Set # | PGS Treatment | Dosage (ppm) | Slip 1 Ht. (in.) | Slip 2 Ht. (in.) | Slip 3 Ht. (in.) |
|---|---|---|---|---|---|---|
|  | 4 | Water |  | 2⅛ | 1¼ | 1¼ |
|  | 3 | BMIA(Br) | 5 | 3 | 1⅞ | 3½ |
|  | 4 | Water |  | 1⅜ | 2⅝ | 2¾ |
| 27 | 1 | BMVE | 5 | 2⅜ | 4¼ | 3⅞ |
|  | 4 | Water |  | 3¼ | 2⅜ | 2⅜ |
|  | 2 | BMTA | 5 | 3⅛ | 3¾ | 3⅞ |
|  | 4 | Water |  | 2½ | 1¾ | 2⅜ |
|  | 3 | BMIA(Br) | 5 | 3⅛ | 3¼ | 4⅛ |
|  | 4 | Water |  | 3½ | 3⅛ | 3⅛ |

TABLE 3-C

| Day | Set # | Treatment | Sum (Slip 1 + 2 + 3) | Ratio: Test/Control | % of Control |
|---|---|---|---|---|---|
| 11 | 1 | BMVE | 8½ | 8.5/6.75 | 125.93% |
|  | 4 | Water | 6¾ |  |  |
|  | 2 | BMTA | 8⅝ | 8.625/4.625 | 186.49% |
|  | 4 | Water | 4⅝ |  |  |
|  | 3 | BMIA(Br) | 8⅜ | 8.375/7.75 | 108.06% |
|  | 4 | Water | 7¾ |  |  |
| 27 | 1 | BMVE | 10½ | 10.5/8 | 131.25% |
|  | 4 | Water | 8 |  |  |
|  | 2 | BMTA | 10¾ | 10.75/6.625 | 162.26% |
|  | 4 | Water | 6⅝ |  |  |
|  | 3 | BMIA(Br) | 10½ | 10.5/9.75 | 107.69% |
|  | 4 | Water | 9¾ |  |  |

Example IV

General Procedure for Bulb Soaking Treatment using Holland Narcissus Bulbs

In this preferred embodiment of the present invention, bulbs are soaked in prepared bio-regulator solutions for two different periods. The first period was two hours. The second period was three and three quarter hours.

The bulbs were selected on November 25, from packets of Dutch Master type bulbs procured from Van Bioem Gardens, located in Meridan, Mississippi, which bulbs are a product of Holland. This selection was meant to be representative of general bulb-type plants and was not meant to be limiting. The selected packet originally contained 26 bulbs, however, the three largest and five smallest were removed and discarded so that the study would only encompass approximately average-sized bulbs. The remaining 18 bulbs were separated into three sets with six approximately equal-sized bulbs per set.

Two of the sets of six bulbs (12 in total) were placed into one sealable container with 20 ounces of bio-regulator solution, which was composed of 5 ppm BMVE and 0.05 ppm Kinetic®. The remaining six bulbs were placed into a second sealable container with 10 ounces of water. Both of the containers were rotated every five to 10 minutes in order to allow for even distribution and absorption of the bio-regulator solution and water respectively.

As mentioned above, after two hours the first set of six bulbs were removed from the container. These bulbs were drained and air-dried. One and three quarter hours later the remaining bulbs were removed from both containers and air-dried. All sets were planted into marked clay pots containing potting soil and subsequently irrigated. The first set of bulbs that soaked for two hours were marked Set 1. The second set of bulbs that soaked three and three-quarter hours were marked Set 2. The bulbs that soaked in water for three and three-quarter hours were marked as the Control group.

The pots were six-inches in diameter and five-inches high. The pots were then placed outdoors and irrigated with water as needed, or according to known practice in the art.

On January 17, bulb shoots began emerging with green foliage. On March 1, measurements were taken of the height of the tallest leaf stalk of each plant (the stalks without a flower). Also, on March 1, measurements were taken of the stalks with flowers, which were found on seven different plants (each of these seven different plants may or may not have had multiple measured stalks). Each stalk that was measured was numbered.

In the study of this embodiment, it was observed that the BMVE treated bulbs showed enhanced growth from the time of planting, through completion of the study. The stalks had observable increased biomass. The enhanced growth observed possibly could have been even more substantial had it not been for "twinning" (where more than one plant is attached) that was observed among the treated bulbs.

This example is summarized in Table 4-A, Table 4-B, and Table 4-C below.

TABLE 4-A (Control treated with water, Set 1 treated with BMVE-two hours, and Set 2 treated with BMVE-three and three-quarter hours): Measurement of Stalks That did not Have Flowers

| Stalk No. | Control | Set 1 | Set 2 |
|---|---|---|---|
| 1 | 6 | 10.25 | 7.5 |
| 2 | 5.75 | 6.625 | 6.875 |
| 3 | 5.5 | 8.875 | 4.875 |
| 4 | 4.5 | 7.125 | 6.375 |
| 5 | 3.125 | 7.5 | 6.375 |
| 6 | 2.1875 | 4.5 | 6.125 |
| 7 | 1.5 | 6.625 | 4.75 |
| 8 | 1.5 | 6.5 | 6 |
| 9 |  | 6.5 | 4.125 |
| 10 |  | 4.625 | 5.625 |
| 11 |  | 6 | 5.25 |
| 12 |  | 4.5 | 4.75 |
| 13 |  | 4.125 | 4.625 |
| 14 |  | 3.375 | 4.625 |
| 15 |  | 7.5 |  |
| Total | 30.0625 | 94.625 | 77.875 |
| Avg. Ht. | 3.76 | 6.31 | 5.56 |

TABLE 4-B

Measurement of Stalks without Flowers and Stalks with Flowers

| | Measurement of Stalk Ht. | | | | Measurement of Stalk Ht. with Flower | | |
|---|---|---|---|---|---|---|---|
| Stalk No. | Control | Set 1 | Set 2 | Stalk No. | Control | N1 | N2 |
| 1 |  |  | 9.5 | 1 | 8.25 | 12.65 |  |
| 2 | 6.625 | 11.625 | 9 | 2 |  |  |  |
| 3 |  |  | 8.875 | 3 | 7.875 | 10.875 |  |
| 4 | 5.5 | 11.375 |  | 4 |  |  | 8.75 |
| 5 |  |  | 8.625 | 5 | 7.75 | 9.625 |  |
| 6 | 6 | 8.125 |  | 6 |  |  | 8.75 |
| 7 | 6.5 | 9.25 | 5.75 | 7 |  |  |  |
| 8 | 6.375 |  |  | 8 |  | 8.875 | 8.375 |
| 9 |  | 7.25 | 8.375 | 9 | 5 |  |  |
| 10 | 2.625 | 6.75 |  | 10 |  |  | 8.25 |
| 11 | 3.875 | 8.5 | 8 | 11 |  |  |  |
| 12 | 3.875 |  | 7.875 | 12 |  | 8.5 |  |
| 13 | 3.5 | 7.5 |  | 13 |  |  | 7.5 |
| 14 |  | 8.5 | 6.25 | 14 |  |  |  |
| 15 |  | 6.75 | 7.375 | 15 |  |  |  |
| 16 |  | 5.125 | 6.5 | 16 |  |  |  |
| Total | 44.875 | 90.75 | 86.125 | Total | 28.88 | 50.5 | 41.625 |
| Avg. Ht. | 4.99 | 8.25 | 7.83 | Avg. Ht. | 7.22 | 10.1 | 8.325 |

TABLE 4-C

Percent of Control (from March 6)

| | Measured Stalks that had no Flower | | | Measured Stalks that did have Flower | | |
|---|---|---|---|---|---|---|
| | No. Stalks | Avg. Ht. | % of Control | No. Stalks | Avg. Ht. | % of Control |
| Control | 9 | 4.99 |  | Control | 4 | 7.22 |  |
| Set 1 | 11 | 8.25 | 165% | Set 1 | 5 | 10.1 | 140% |
| Set 2 | 11 | 7.83 | 157% | Set 2 | 5 | 8.325 | 115% |

Example V

General Procedure for Seed Soaking Treatment of Agricultural Crops Using Radish Seeds In this preferred embodiment of the present invention, seeds were soaked in prepared bio-regulator solutions for a period of three hours. Radish seeds were selected from a local nursery (September 28). This selection was not meant to be limiting but was meant to be a selection of a typical California radish seed. Two bio-regulator solutions were prepared. The first bio-regulator solution was prepared using 5 ppm BMVE solution combined with 0.05% v/v Kinetic®. The second bio-regulator solution was prepared using 3 ppm BMIA in water and Kinetic® solution. The solution was drained and the seeds planted in marked clay pots with potting soil. The clay pots were four inches high and six inches in diameter. Three sets of two pots were set up for this study; one set for the test group with BMVE treatment, one set for the test group with BMIA treatment and one set for the control group.

On January 1, a visual review of all of the radish tops was conducted. It was observed that all three sets of plants were very close in vigor and chlorophyll green. Then the radish plants were removed from clay pots for root evaluation. The treated plants showed an increased number of fine roots as compared to the control plants. The radish plants were clipped, cleaned and weighed for a more accurate determination of treatment effects.

The results showed that the treated radish plants had increased biomass. The study of this embodiment is summarized in Table 5-A below, and the results are summarized in Table 5-B.

TABLE 5-A

| Treatment | PPM | Soak Time (hrs) | Surfactant | Location |
|---|---|---|---|---|
| Water | 0 | 3 | Kinetic® | Outdoor |
| BMVE | 5 | 3 | Kinetic® | Outdoor |
| BMIA | 3 | 3 | Kinetic® | Outdoor |

TABLE 5-B

| Treatment | Weight (gm) |
|---|---|
| Water | 11 |
| BMVE | 17 |
| BMIA | 12 |

Example VI

General Procedure for Seed Soaking Treatment of Agricultural Crops Using Lemon Seeds In this preferred embodiment of the present invention, seeds were soaked in prepared bio-regulator solutions for a period of three hours. Lemon seeds were selected from Eureka Lemon Tree (January 5). This selection was not meant to be limiting but was meant to be a selection of a typical lemon seed. The lemon seeds were separated into three sets with seven seeds in each set The first set, Set 1, was the control set, and was soaked in water with Kinetic® surfactant. The second set, Set 2, soaked in BMVE solution with Kinetic® surfactant. The third set, Set 3, soaked in BMIA solution with Kinetic® surfactant. The seeds were dried and planted.

The seeds were observed until sprouts appeared. When sprouts began to grow, sprouts were selected from each pot with lengths approximately three inches long. These sprouts were transplanted to pots that were six-inches in diameter, and seven inches tall. These pots were placed outdoors. A month after the initial planting, the test study was duplicated.

The results showed that the treated plants had increased roots, sprouts, and overall biomass as compared to the control. The study of this embodiment is summarized in Table 6-A, and in Table 6-B. The overall results are summarized in Table 6-C.

TABLE 6-A

| | Treatment | PPM | Soak Time |
|---|---|---|---|
| Set 1 | Water | 0 | 3 hrs |
| Set 2 | BMVE | 5 | 3 hrs |
| Set 3 | BMIA | 3 | 3 hrs |

TABLE 6-B

| Set # | Date | Treatment | Sprouts | Description |
|---|---|---|---|---|
| Set 1 | 24 Feb | Water | 0 | |
| Set 2 | 24-Feb | BMVE | 0 | |
| Set 3 | 24-Feb | BMIA | 2 | 5 and 12 mm long |
| Set 1 | 1-Mar | Water | 2 | 5 and 5 mm long |
| Set 2 | 1-Mar | BMVE | 0 | |

TABLE 6-B-continued

| Set # | Date | Treatment | Sprouts | Description |
|---|---|---|---|---|
| Set 3 | 1-Mar | BMIA | 3 | sprouts with roots |
| Set 1 | 4-Mar | Water | 3 | sprouts with roots |
| Set 2 | 4-Mar | BMVE | 0 | |
| Set 3 | 4-Mar | BMIA | 7 | sprouts with roots |

TABLE 6-C

| Date | Planting | Control | BMVE | BMIA | % of Control (BMVE) | % of Control (BMIA) |
|---|---|---|---|---|---|---|
| 22-Aug | 1st | 5.125 | 8.625 | 7.5 | 168% | 146% |
| 22-Aug | 2nd | 4.875 | 5.875 | 6.375 | 121% | 131% |
| 20-Sep | 1st | 7.75 | 12.125 | 9.875 | 156% | 127% |
| 20-Sep | 2nd | 7.5 | 8.125 | 9 | 108% | 120% |
| 21-Nov | 1st | 8.5 | 16 | 13.75 | 188% | 162% |
| 21-Nov | 2nd | 9.75 | 11.5 | 12 | 118% | 123% |

Example VII

General Procedure for Seed Soaking Treatment of Agricultural Crops Using Cotton Seeds In this preferred embodiment of the present invention, seeds were soaked for a period of 3 hours in the bio-regulator solution. Cotton Bt were selected and studied to determine if bio-regulator chemistry will enhance or influence the inserted Bt genes of the transgenic plant. The seeds were separated into two different sets on July 2. The first set, Set 1, was soaked in 5 ppm BMPA solution with 0.05% Kinetic®. The second set, Set 2, was soaked in water with 0.05% v/v Kinetic®.

The solution was drained and the treated seeds planted in starter plastic trays. After germination and after the seedlings reached the height of four inches, the cotton Bt plants were transplanted into larger six-inch plastic containers. The cotton plants were placed outdoors for the duration of the study. The different sets of plants were regularly observed throughout this study.

After 47 days from planting, it was noted that the underside of the leaf of the untreated cotton Bt plant showed traces of aphid infestation. No trace of aphid was observed on the treated cotton Bt plant, which was placed 20 inches from the untreated cotton Bt plant.

After 55 days from planting, it was noted that the aphid infestation of the untreated cotton Bt plant was heavy and the plant was beginning to show stress. No aphid was found on the treated cotton Bt plant. After 57 days from planting, it was noted that a few aphids were detected on the treated plant. After 74 days from planting, it was noted that the treated plant appeared to be infested with aphid and showing some stress.

For the study of this embodiment, the treatment using the bio-regulator chemistry (BMPA) appears to delay the infestation of aphids on the cotton Bt plant by as much as 19 days. The study for this embodiment is summarized in Table 7-A below, and the results are summarized in Table 7-B.

TABLE 7-A

| | Treatment | PPM | Soak Time | Surfactant |
|---|---|---|---|---|
| Set 1 | Water | 0 | 3 hrs | Kinetic® |
| Set 2 | BMPA | 5 | 3 hrs | Kinetic® |

TABLE 7-B

| Days After Planting | Control | Treated |
|---|---|---|
| 47 | L-Aphid | No Aphid |
| 55 | H-Aphid | No Aphid |
| 57 | H-Aphid | L-Aphid |
| 74 | Stressed | M-Aphid |

Key:
L—light infestation;
M—medium infestation;
H—heavy infestation;
Stressed—overcome by infestation In this example, the effect of the bio-regulator solution on cotton seed was studied. However, it is anticipated that similar effects, results, and outcomes will be achievable following a similar procedure as outlined above for plants in the *Gossypium* genus.

Example VIII

General Procedure for Treatment of Agricultural Crops Using Soybeans

Spray Tests

In this preferred embodiment of the present invention, three seeds each of soybean varieties Thorn (non-Roundup Ready variety) or S30-D4 (Syngenta Roundup Ready variety) were sown in 6 inch pots (50 total pots with 3 seeds each per variety) containing soybean potting mix (40% Canadian Peat, 40% Coarse Vermiculite, 15% Masonry Sand, 5% Screened Topsoil, 3.63% Waukesha fine lime, 0.46% Micromax, 0.68% AquaGro, and 0.23% Hi Yield Iron Plus). Pots were placed in the greenhouse growth regime initially set at 29° C., 14-hour days and 24° C., 10-hour nights (23 days after planting (DAP), the growth regime was set at 25° C., 14-hour days and 15° C., 10-hour nights). Plants were watered on Monday, Wednesday, and Friday. The plant irrigation schedule involved alternating plain water, 500 ppm Ca, and 350 ppm N and 60 ppm Fe. Following emergence and cotyledon expansion, plants were thinned to one plant per pot. A significant number of the Thorn soybean plants derived from the seeds provided by UNL Beadle Center were abnormal and, overall, the plants showed a significant lack of uniformity with regards to development. Therefore, work on the Thorn soybean plants was discontinued. S30-D4 soybean plants were sprayed with 1 or 3 ppm BMVE in 0.05% Tween 20 or 0.05% Tween 20 (control) at the first trifoliate leaf stage, the fifth trifoliate leaf stage and the R1 (flowering) stage of development (3, 7 and 10 sprays per plant to ensure complete plant coverage at the first trifoliate, fifth trifoliate and flowering stages, respectively). At 34 DAP, five of the ten replications of soybean plants previously treated with foliar applications of the control, BMVE 1 ppm, and BMVE 3 ppm treatments at the first and fifth trifoliate leaf and flowering stages were irrigated at a rate of 1 L per pot with 100 mM of NaCl in either 350 ppm N and 60 ppm Fe (Monday), water (Wednesday), or 500 ppm Ca (Friday), while the remaining 5 replicas were irrigated similarly except that NaCl was excluded. At flowering plant leaf tissue from saline stressed and non-stressed plants were sampled for extraction of RNA to be used in Illumina and/or microarray analyses.

Over the course of soybean plant development, measurements were made to assess phenotypes as related to the foliar treatments. Plant height, leaf expansion, internode length, rate of photosynthesis, leaf chlorophyll content, and flowering and pod production time data are provided below in the Results section.

Seed Soak Tests

In another preferred embodiment of the present invention, Syngenta S30-D4 soybean seeds were soaked in water or 0.05% Tween 20 (controls) or BMVE at 1, 3, and 6 ppm in 0.05% Tween 20 and then planted in 6 inch pots containing soybean potting mix. Following emergence and expansion of the first trifoliate leaves, plants were thinned to one plant per pot. These experiments are currently ongoing.

Observations

Spray Tests

Table 8-A shows mean height, leaf expansion, and internode length values of S30-D4 soybean plants following foliar applications with 0.05% Tween 20 (control), or 1 or 3 ppm BMVE in 0.05% Tween 20 (BMVE 1 ppm and BMVE 3 ppm, respectively). Ten replications of 4 S30-D4 soybean seeds were planted in 6 inch pots in the greenhouse at a growth regime initially set at 29° C., 14-hour days and 24° C., 10-hour nights (twenty-three days after planting (DAP), the growth regime was set at 25° C., 14-hour days and 15° C., 10-hour nights). Following full expansion of the first trifoliate leaf, seedlings were thinned to one plant per pot and the remaining 50 seedlings appeared uniform in size and development. At the first and fifth trifoliate leaf and at flowering, foliar control, BMVE 1 ppm, and BMVE 3 ppm treatments were applied with a spray bottle (3, 7 and 10 sprays per plant to ensure complete plant coverage at the first trifoliate, fifth trifoliate and flowering stages, respectively). Plant heights and leaf expansion measurements were taken at the fifth trifoliate leaf stage and internode lengths were recorded at the initiation of flowering.

In at least one embodiment where S30-D4 soybean plants received foliar applications at the first and fifth trifoliate leaf stage of BMVE at a concentration of 3 ppm in 0.05% Tween 20. The plants showed increased plant height as compared to a control treated with 0.05% Tween 20.

TABLE 8-A

| | Plant Height | | Leaf Expansion in cm (middle lobe of the $5^{th}$ trifoliate leaf) 30 DAP | | | | Internode Length in cm ($4^{th}$ to $5^{th}$ node) 41 DAP | |
|---|---|---|---|---|---|---|---|---|
| | (cm) 29 DAP | | L | L | W | W | | |
| | Mean | StDev | Mean | StDev | Mean | StDev | Mean | StDev |
| control | 21.08 | 2.95 | 10.70 | 0.46 | 6.67 | 0.53 | 2.51 | 0.35 |
| B 1 ppm | 22.35 | 1.61 | 10.83 | 0.63 | 7.25 | 0.38 | 2.71 | 0.31 |
| B 3 ppm | 24.77 | 2.01 | 10.86 | 0.53 | 7.11 | 0.37 | 3.41 | 0.45 |

Photosynthesis Rate

Table 8-B shows mean and standard deviation from the mean of rates of photosynthesis obtained by quantifying decrease of $CO_2$ over time inside a leaf chamber enclosing 6 $cm^2$ of leaf tissue from the middle lobe of the fifth trifoliate leaf of S30-D4 soybean plants with a LI-6400XT infrared gas analyzer following two foliar applications with 0.05% Tween 20 (control), or BMVE at a concentration of 1 or 3 ppm in 0.05% Tween 20 (BMVE 1 ppm and BMVE 3 ppm, respectively). Ten replications of 4 S30-D4 soybean seeds were planted in 6 inch pots in the greenhouse at a growth regime initially set at 29° C., 14-hour days and 24° C., 10-hour nights (twenty-three days after planting (DAP), the growth regime was set at 25° C., 14-hour days and 15° C., 10-hour nights).

Following emergence and development of the first trifoliate leaf, seedlings were thinned to one plant per pot and the remaining 50 seedlings appeared uniform in size and development. Upon full expansion of the first trifoliate and fifth trifoliate leaf, foliar control, BMVE 1 ppm, and BMVE 3 ppm treatments were applied with a spray bottle (3 and 7 sprays per plant to ensure complete plant coverage at the first and fifth trifoliate stages, respectively). Photosynthetic rates were determined with the LI-6400XT at the fifth trifoliate leaf stage at 29 DAP.

TABLE 8-B

| Treatment | Photosynthetic rate (decrease in $CO_2$ over time in chamber enclosing fixed leaf area - $\mu mol\ CO_2/m^2/sec$) | |
|---|---|---|
| | Mean | StDev |
| Control | 16.7 | 1.4 |
| B 1 ppm | 17.0 | 0.9 |
| B 3 ppm | 15.9 | 2.2 |

Chlorophyll Content

Table 8-C shows mean and standard deviation from the mean of relative chlorophyll content measured with a Minolta SPAD 502 chlorophyll meter on the uppermost, fully expanded trifoliate leaf of S30-D4 soybean plants following three foliar applications with 0.05% Tween 20 (control), or 1 or 3 ppm BMVE in 0.05% Tween 20 (BMVE 1 ppm and BMVE 3 ppm, respectively). Ten replications of 4 S30-D4 soybean seeds were planted in 6 inch pots in the greenhouse at a growth regime initially set at 29° C., 14-hour days and 24° C., 10-hour nights (23 days after planting (DAP), the growth regime was set at 25° C., 14-hour days and 15° C., 10-hour nights). Following full expansion of the first trifoliate leaf, seedlings were thinned to one plant per pot and the remaining 50 seedlings appeared uniform in size and development. At the first and fifth trifoliate leaf stage and at flowering, foliar control, BMVE 1 ppm, and BMVE 3 ppm treatments were applied with a spray bottle (3, 7 and 10 sprays per plant for complete plant coverage at the first trifoliate, fifth trifoliate and flowering stages, respectively). At 34 DAP, five of the ten replications previously treated with foliar applications of control, BMVE 1 ppm, and BMVE 3 ppm treatments at the first and fifth trifoliate leaf and flowering stages were irrigated at a rate of 1 L per pot with 100 mM of NaCl in either 350 ppm N and 60 ppm Fe (Monday), water (Wednesday), or 500 ppm Ca (Friday), while the remaining 5 replicas were irrigated similarly except that NaCl was excluded. Chlorophyll contents were measured at 49 DAP.

TABLE 8-C

| | Chlorophyll Content - Saline Stress | | Chlorophyll Content - No Stress | |
|---|---|---|---|---|
| Treatment | Mean | St Dev | Mean | St Dev |
| Control | 37.5 | 2.0 | 37.8 | 1.6 |
| B 1 ppm | 37.3 | 1.9 | 38.3 | 1.3 |
| B 3 ppm | 37.7 | 1.5 | 39.5 | 1.6 |

Flowering Nodes

Figure 6A:
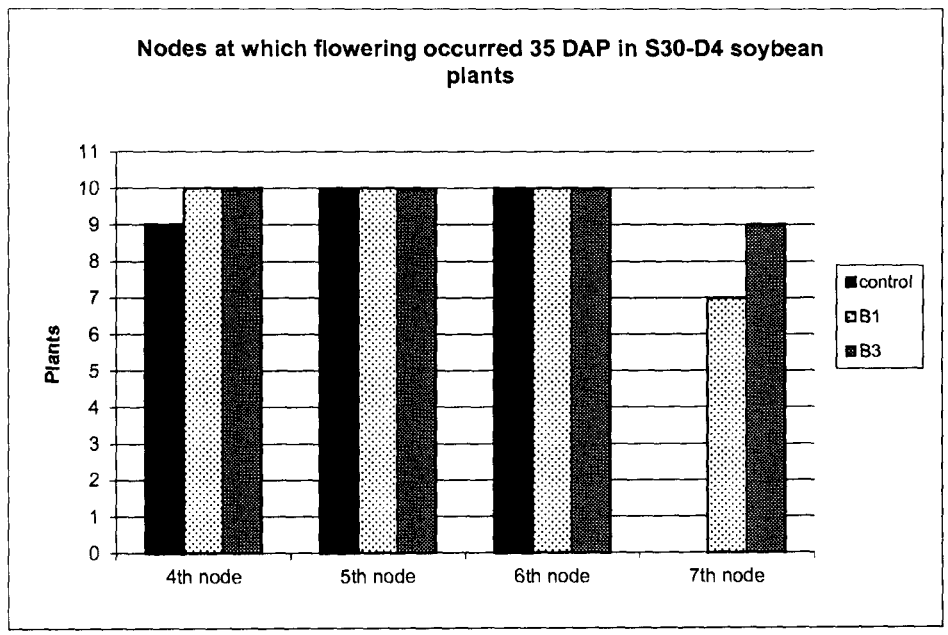
FIG. 6a shows nodes at which flowering occurred in plants treated with embodiments of the present invention.
Figure 6B:
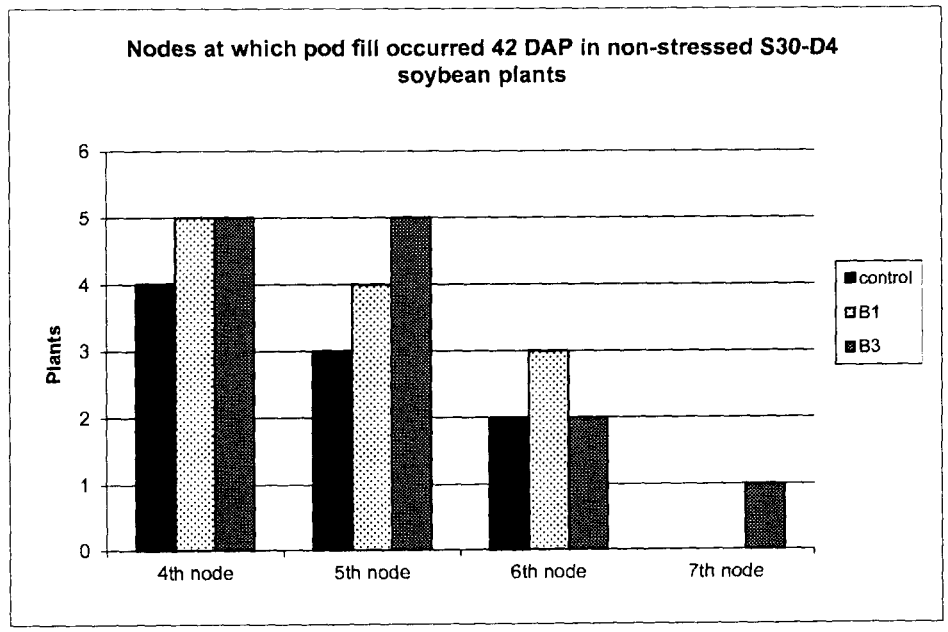
FIG. 6b shows nodes at which flowering occurred in plants treated with embodiments of the present invention.

FIGs. 6a and 6b illustrates nodes at which flowering occurred in S30-D4 soybean plants following foliar applications with 0.05% Tween 20 (control), or 1 or 3 ppm BMVE in 0.05% Tween 20 (BMVE 1 ppm (B1 in FIGs. 6a and 6b))and BMVE 3 ppm (B3 in FIGs. 6a and 6b), respectively). Ten replications of 4 S30-D4 soybean seeds were planted in 6 inch pots in the greenhouse at a growth regime initially set at 29° C., 14-hour days and 24° C., 10-hour nights (23 days after planting (DAP), the growth regime was set at 25° C., 14-hour days and 15° C., 10-hour nights). Following full expansion of the first trifoliate leaf, seedlings were thinned to one plant per pot and the remaining 50 seedlings appeared uniform in size and development. Upon full expansion of the first trifoliate, fifth trifoliate leaf and at flowering, foliar control, BMVE 1 ppm, and BMVE 3 ppm treatments were applied with a spray bottle (3, 7 and 10 sprays per plant to ensure complete plant coverage at the first trifoliate, fifth trifoliate and flowering stages, respectively). Flowering data was recorded 35 DAP.

Figure 7:
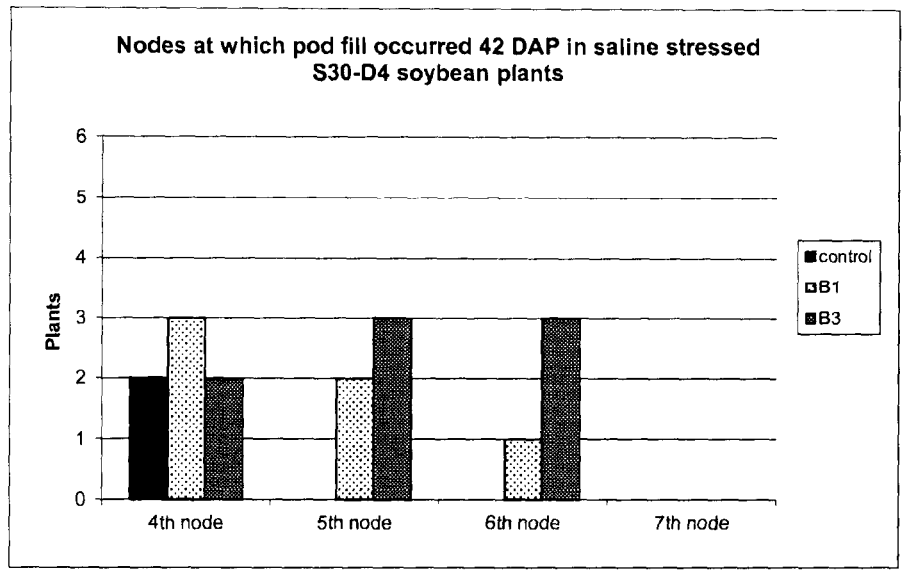
FIG. 7 shows nodes at which pod formation occurred in plants treated with embodiments of the present invention.

FIG. 7 shows nodes at which pod formation occurred in S30-D4 soybean plants following foliar applications with 0.05% Tween 20 (control), or 1 or 3 ppm BMVE in 0.05% Tween 20 (BMVE 1 ppm (B1 in FIG. 7) and BMVE 3 ppm (B3 in FIG. 7), respectively). Ten replications of 4 S30-D4 soybean seeds were planted in 6 inch pots in the greenhouse at a growth regime initially set at 29° C., 14-hour days and 24° C., 10-hour nights (twenty-three days after planting (DAP), the growth regime was set at 25° C., 14-hour days and 15° C., 10-hour nights). Following full expansion of the first trifoliate leaf, seedlings were thinned to one plant per pot and the remaining 50 seedlings appeared uniform in size and development. Upon full expansion of the first trifoliate, fifth trifoliate leaf and at flowering (31 DAP), foliar control, BMVE 1 ppm, and BMVE 3 ppm treatments were applied with a spray bottle (3, 7 and 10 sprays per plant to ensure complete plant coverage at the first trifoliate, fifth trifoliate and flowering stages, respectively). At 34 DAP, five of the ten replications of soybean plants previously treated with foliar applications of the control, BMVE 1 ppm, and BMVE 3 ppm treatments at the first and fifth trifoliate leaf and flowering stages were irrigated at a rate of 1 L per pot with 100 mM of NaCl in either 350 ppm N and 60 ppm Fe (Monday), water (Wednesday), or 500 ppm Ca (Friday) (pod fill data in panel B), while the remaining 5 replicas were irrigated similarly except that NaCl was excluded (pod fill data in panel A). Pod formation data was recorded 42 DAP.

Saline Stress

Table 8-G shows mean and standard deviation from the mean of plant height measurements on saline stressed and non-stressed S30-D4 soybean plants following three foliar applications with 0.05% Tween 20 (control), or 1 or 3 ppm BMVE in 0.05% Tween 20 (BMVE 1 ppm and BMVE 3 ppm, respectively). Ten replications of 4 S30-D4 soybean seeds were planted in 6 inch pots in the greenhouse at a growth regime initially set at 29° C., 14-hour days and 24° C., 10-hour nights (23 days after planting (DAP), the growth regime was set at 25° C., 14-hour days and 15° C., 10-hour nights). Following full expansion of the first trifoliate leaf, seedlings were thinned to one plant per pot and the remaining 50 seedlings appeared uniform in size and development. At the first and fifth trifoliate leaf stage and at flowering, foliar control, BMVE 1 ppm, and BMVE 3 ppm treatments were applied with a spray bottle (3, 7 and 10 sprays per plant for complete plant coverage at the first trifoliate, fifth trifoliate and flowering stages, respectively). At 34 DAP, five of the ten replications previously treated with foliar applications of control, BMVE 1 ppm, and BMVE 3 ppm treatments at the first and fifth trifoliate leaf and flowering stages were irrigated at a rate of 1 L per pot with 100 mM of NaCl in either 350 ppm N and 60 ppm Fe (Monday), water (Wednesday), or 500 ppm Ca (Friday), while the remaining 5 replicas were irrigated similarly except that NaCl was excluded. Chlorophyll contents were measured at 49 DAP.

TABLE 8-G

| Treatment | Plant Height (cm) - Saline Stressed | | Plant Height (cm) - No Stress | |
| --- | --- | --- | --- | --- |
| | Mean | St Dev | Mean | St Dev |
| Control | 40.8 | 1.1 | 46.4 | 2.1 |
| B 1 ppm | 44.6 | 3.6 | 54.0 | 2.5 |
| B 3 ppm | 44.2 | 3.4 | 58.0 | 8.6 |

Table 8-H shows mean and standard deviation from the mean of leaf area measurements on saline stressed and non-stressed S30-D4 soybean plants following three foliar applications with 0.05% Tween 20 (control), or 1 or 3 ppm BMVE in 0.05% Tween 20 (BMVE 1 ppm and BMVE 3 ppm, respectively). Ten replications of 4 S30-D4 soybean seeds were planted in 6 inch pots in the greenhouse at a growth regime initially set at 29° C., 14-hour days and 24° C., 10-hour nights (23 days after planting (DAP), the growth regime was set at 25° C., 14-hour days and 15° C., 10-hour nights). Following full expansion of the first trifoliate leaf, seedlings were thinned to one plant per pot and the remaining 50 seedlings appeared uniform in size and development. At the first and fifth trifoliate leaf stage and at flowering, foliar control, BMVE 1 ppm, and BMVE 3 ppm treatments were applied with a spray bottle (3, 7 and 10 sprays per plant for complete plant coverage at the first trifoliate, fifth trifoliate and flowering stages, respectively). At 34 DAP, five of the ten replications previously treated with foliar applications of control, BMVE 1 ppm, and BMVE 3 ppm treatments at the first and fifth trifoliate leaf and flowering stages were irrigated at a rate of 1 L per pot with 100 mM of NaCl in either 350 ppm N and 60 ppm Fe (Monday), water (Wednesday), or 500 ppm Ca (Friday), while the remaining 5 replicas were irrigated similarly except that NaCl was excluded. Leaf area measurements were estimated on the trifoliate leaf from the seventh node with (SigmaScan Pro 5.0, Systat Software Inc., Point Richmond, Calif.).

TABLE 8-H

| Treatment | Leaf Area - Saline Stressed | | Leaf Area - No Stress | |
| --- | --- | --- | --- | --- |
| | Mean | St Dev | Mean | St Dev |
| Control | 163.1 | 12.0 | 167.0 | 15.1 |
| B 1 ppm | 188.7 | 23.6 | 186.7 | 14.6 |
| B 3 ppm | 191.0 | 6.9 | 172.1 | 17.1 |

3. Results and Conclusions:

Based on studies of these embodiments, foliar treatment of S30-D4 soybean plants with BMVE at 1 and 3 ppm appeared to increase the rate of plant growth and development in saline stress and non-stress regimes; increases were particularly notable at the 3 ppm rates. Based on the measurements taken with the Minolta SPAD 502 meter and the Li-6400XT infrared gas analyzer in this investigation, chlorophyll content likely was not increased per unit area by the bio-regulator chemistries. However, an increase in total photosynthetic capacity per plant is likely given that overall vegetative matter/leaf surface area was increased.

Example IX

General Procedure for Seed Soaking Treatment of Agricultural Crops Using Corn Seeds In a preferred embodiment of the present invention, corn seeds were treated with 5 ppm BMVE. Corn seeds were treated and germinated in the Martinez, Calif., greenhouse. After seedlings reached heights of four inches tall, seedlings were placed outdoors for the remaining period of study. After seedlings reached 8 to 12 inches, they were exposed to temperatures exceeding 100 degrees Fahrenheit for several days (ranges were from 100 to 115 degrees F.). The treated corn seedlings continued healthy growth under these conditions while the control seedlings did not survive.

The results of the study of this embodiment showed that the treated plants had increased roots, sprouts, and overall biomass as compared to the control. The study that encompasses this example is summarized in Table 9.

TABLE 9

| Location | Planted | Photo | Treatment | Dosage (ppm) | Temp (degrees F.) |
| --- | --- | --- | --- | --- | --- |
| Greenhouse | Aug 26 | | BMVE | 5 | 80 |
| Out door | | Sept. 15 | | | 115 |

Example X

General Procedure for Seed Soaking Treatment of Agricultural Crops Using Watermelon Seeds In this preferred embodiment of this invention, watermelon seeds were treated with BMVE and planted alongside untreated seeds (control). From an early seedling stage, the treated growth plants increased height as well as foliage. The watermelon fruits of the treated were observably larger than the control, the largest fruit form the treated plant weighed 16 pounds vs. 11 pounds for the largest control.

The results of the study of this embodiment showed that the treated plants had increased overall biomass as compared to the control. The study that encompasses this example is summarized in Table 10.

TABLE 10

| Date of Planting | Treatment | Dosage (ppm) | Date of Harvest | Wt. of Melon (lbs) |
|---|---|---|---|---|
| May 18 | BMVE | 5 | Sept. 20 | 16 |
| May 18 | Water | 0 | Sept. 20 | 11 |

Example XI

General Procedure for Seed Soaking Treatment of Agricultural Crops Using Sunflower Seeds In this preferred embodiment of the present invention, sunflower seeds were selected from the Melody variety and were soaked for three hours in solutions containing 0.05% Tween 20 and BMTA or BMPA, at a concentration of 3 ppm. Another group of seeds of the same variety was soaked in a solution with only in 0.05% Tween 20 added (control). Following soaking, seeds were desiccated to storage moisture contents and BMTA, BMPA and control seeds were sown in three twenty-five foot plots (Reps) each on May 21 (plots were arranged in a randomized block design). On September 16, sunflower heads were harvested, with a harvest of around 20 heads per plot/Rep on average. The heads were hand-threshed to collect seeds. Moisture, count, and weight data was collected on seeds from each head.

The results of the study of this embodiment showed that the treated plants generally had increased moisture, seed count, and overall plant yield. The results from this example are encompassed in Table 11-A, and Table 11-B. Table 11-A shows mean seed moisture contents (% moisture), fresh seed weights, seed counts, seed weights at 6% moisture content (Wt. at 6% Moist; all data normalized to 6% seed moisture content to obtain yield data), and yield estimates in pounds based on planting rate of 20,000 seeds/acre for each Rep. Table 11-B shows the mean of the data presented in Table 11-A over the three Reps for each treatment.

TABLE 11-A

| Treatment | Rep | % Moist | Fresh Seed Wt. (gm) | Seed Count | Wt. at 6 % Moist | Yield @ 20,000 Plants/Acre (lbs) |
|---|---|---|---|---|---|---|
| Control | 1 | 10.56 | 64.75 | 1081 | 61.54 | 2711 |
|  | 2 | 12.00 | 68.98 | 1065 | 64.01 | 2820 |
|  | 3 | 15.04 | 62.68 | 1041 | 56.68 | 2497 |
| BMTA | 1 | 13.10 | 77.35 | 1226 | 71.43 | 3147 |
|  | 2 | 13.01 | 73.58 | 1157 | 67.86 | 2989 |
|  | 3 | 14.82 | 61.64 | 942 | 55.94 | 2464 |
| BMPA | 1 | 13.52 | 78.24 | 1185 | 71.99 | 3171 |
|  | 2 | 13.93 | 65.01 | 977 | 59.42 | 2617 |
|  | 3 | 12.37 | 65.99 | 1052 | 61.46 | 2708 |

TABLE 11-B

| Treatment | % Moist | Fresh Seed Wt (g) | Seed Count | Wt at 6% Moist | Yield @ 20,000 Plants/Acre (lbs) |
|---|---|---|---|---|---|
| control | 12.53 | 65.47 | 1062 | 60.74 | 2676 |
| BMTA | 13.64 | 70.85 | 1108 | 65.08 | 2867 |
| BMPA | 13.27 | 69.75 | 1071 | 64.29 | 2832 |

Example XII

General procedure for Seed Soaking Treatment of Agricultural Crops Using Onion Seeds In this preferred embodiment of the present invention, approximately sixty onion seeds were soaked for three hours in water or solution containing the KamTec bio-regulator BMCPA. Following soaking, five seeds from each seed soak treatment were sown in ten 5-inch pots (5 seeds each in 10 total pots per seed soak treatment) containing Metro-Mix 200. Pots containing seeds and Metro-Mix 200 media were randomized within seed soak treatment (10 reps in a randomized block design) on a greenhouse bench and watered daily to saturation in a growth regime set at 25° C., 14-hour days and 15° C., 10-hour nights. On Mondays and Fridays pots were fertilized with Peter's 20-10-20 at a rate of 250 ppm.

On days plants weren't fertilized, pots were saturated with water adjusted to pH 6.8. Following about three weeks, pots were thinned to one plant per pot. Onion plants were harvested 47 days after planting. Digital images show each of the ten onion plants derived from the water ($H_2O$—left panel) and bio-regulator (right panel) seed soak treatments.

The results from a study of this embodiment generally showed increase plant and root biomass. The results also showed increased yields as compared to control groups. These results are visible in Table 12.

TABLE 12

Table 12, Mean root and shoot dry weights in grams on five N60G and N73N corn plants 27 days after planting

|  |  | Control | A 1 ppm | B 1 ppm | A 3 ppm | B 3 ppm | A 6 ppm | B 6 ppm |
|---|---|---|---|---|---|---|---|---|
| N60G | Roots | 0.550 | 0.487 | 0.786 | 0.689 | 0.593 | 0.631 | 0.705 |
|  | Shoots | 2.064 | 1.479 | 2.312 | 2.447 | 1.720 | 2.065 | 2.214 |
|  | Root/Shoot | 0.268 | 0.331 | 0.357 | 0.301 | 0.349 | 0.312 | 0.369 |
| N73N | Roots | 0.803 | 1.100 | 0.854 | 0.921 | 0.897 | 1.302 | 0.879 |
|  | Shoots | 3.583 | 4.185 | 3.391 | 2.936 | 3.426 | 4.979 | 3.186 |
|  | Root/Shoot | 0.227 | 0.284 | 0.260 | 0.315 | 0.268 | 0.282 | 0.286 |

Example XIII

General procedure for Seed Soaking Treatment of Agricultural Crops Using Tomato Seeds In a preferred embodiment of the present invention, tomato seeds are treated with 3 ppm BMVE, and soaked for three hours before planting. In a study of this embodiment, tomato seeds were treated and germinated in the Cameron Highlands of Malaysia. Two months after planting, the plants were observed and compared to a control group.

The results of the study of this embodiment showed that the treated plants had increased roots, sprouts, and overall biomass as compared to the control. The study that encompasses this example is summarized in Table 13.

TABLE 13

| Date planted | Date Observed | Treatment | Dosage (ppm) | Soak time (hrs) |
|---|---|---|---|---|
| May 23 | Jul 23 | BMVE | 3 | 3 |

Example XIV

General procedure for Seed Treatment of Agricultural Crops Using Wheat Seed

In this preferred embodiment of the present invention, bio-regulator solutions can be used with fungicides and insecticides. The bio-regulator solution can be tank-mixed with most seed protection products provided such products are miscible in water and labeled for slurry application directly on seed. Compatibility can be checked by mixing a small amount of each product together to confirm suitability of slurry application prior to application.

In another embodiment, the bio-regulator solutions can also be used with biological products. They can be sequentially or simultaneously applied with most biological products when mixed in separate mix tanks. Direct tank-mixing or mixing the bio-regulator solution in the same tank with biological products such as legume inoculants, beneficial fungus, and other live microorganisms is not recommended as the bio-regulator solution might reduce the viability of the micro-organisms with directly mixed slurries. Preferred amounts used in these embodiments are three ounces per 100 pounds of seed.

Studies of these embodiments were carried out in the following locations: Imperial, Nebr.; Colby, Kans.; Manter, Kans.; Newton, Kans.; Osborne, Kans.; Palmer, Kans.; Sedgwick, Kans.; and, Enid, Okla. At each of these locations soil analysis was performed and various characteristics including, but not limited to, pH and mineral content, were recorded. These studies also included seed from the following varieties: WB-Armour, AP-Art, WB-Cedar, WB-Santa Fe, KSU Foundation Everest, WB-Hitch (later maturity), and WB-Winter Hawk (later maturity).

Figure 8:
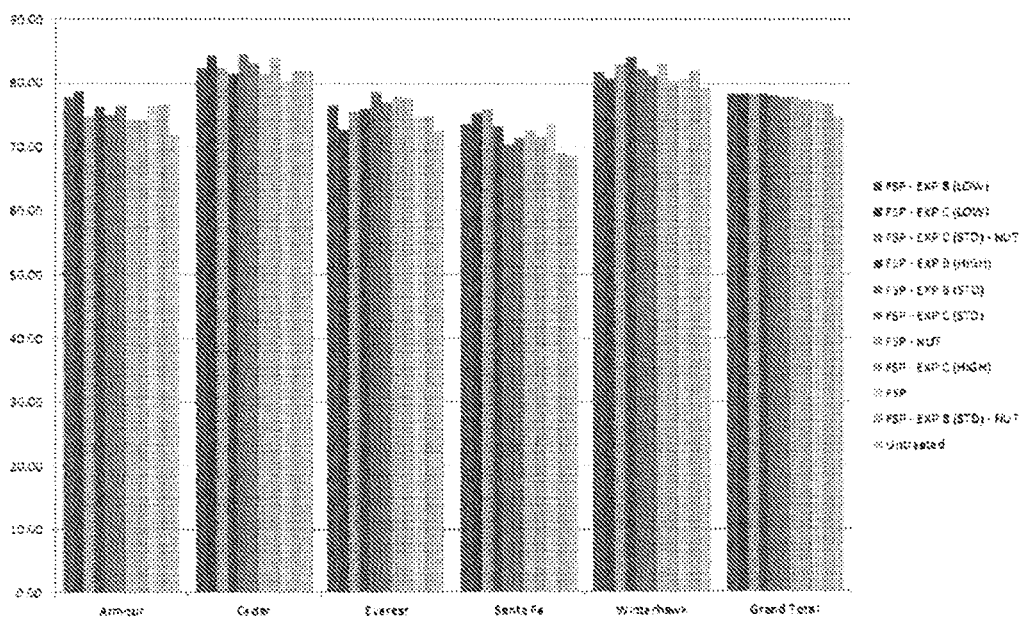
FIG. 8 shows yields from a number of the locations in units of bushels of a study including embodiments of the present invention.

The results of the study of this embodiment showed that the treated plants had increased overall yield and biomass as compared to the control. The study that encompasses this example is summarized in FIG. 8. FIG. 8 includes yields from each of the locations in units of bushels.

2. General Procedure for Seed Soaking Treatment of for Growth Inhibition of Agricultural Crops and Flora Seeds:

In a preferred embodiment of the present invention, amounts or concentrations of the Ester Compounds, the BMIA Compounds, or the Salt Compounds are added to bio-regulatory solution in excess of those amounts for growth enhancement. In another embodiment, amounts or concentrations of the Ester Compounds, the BMIA Compounds, or the Salt Compounds are added to bio-regulatory solution to encourage a detrimental gene expression in a particular environment during burndown. In another embodiment, said compositions are combined with herbicides in order to enhance the effects of the herbicides during burndown.

Example XV

Objective

In this preferred embodiment of the present invention, non-Roundup Ready NE3001 soybean plants were treated with BMVE and glyphosate for the purpose of determining whether BMVE could enhance the effects of glyphosate on glyphosate-susceptible plants. These observations will be useful in burndown scenarios.

Methods

Non-Roundup Ready soybean variety, NE3001 (NE3001 seeds were supplied by Dr. Tom Clemente of the UNL Plant Transformation Core Research Facility). Seeds were sown into 224 5 inch pots (224 total pots with 4 seeds each) containing soybean potting mix (37.5% Canadian Peat, 37.5% Coarse Vermiculite, 15% Masonry Sand, 5% Screened Topsoil, 3.63% Waukesha fine lime, 0.46% Micromax, 0.68% AquaGro, and 0.23% Hi Yield Iron Plus). Pots were placed on benches inside a UNL Beadle Center greenhouse bay set at 25° C., 14-hour days and 15° C., 10-hour nights. Pots were watered on Monday, Wednesday, and Friday. The irrigation schedule involved alternating water, 500 ppm Ca, and 350 ppm N and 60 ppm Fe.

Two hundred and twenty-four pots were sown. At final stand, low seedling emergence/normal seedling percentages were apparent over the 224 pots. Empty pots and pots containing abnormal seedlings were discarded. Pots containing multiple normal seedlings were used for transplanting purposes. Following transplanting, pots containing normal seedlings at similar stages of development were thinned to one plant per pot. Following the selection and transplanting process only 76 pots containing normal seedlings remained. Of the 76 pots, 64 were utilized in a spray table test.

NE3001 soybean plants at the sixth trifoliate leaf stage were sprayed on a spray table set to apply either 0.05% Tween 20, 5 ppm BMVE and 0.05% Tween 20, 50 ppm BMVE and 0.05% Tween 20, 100 ppm BMVE and 0.05% Tween 20, 5 ppm BMVE and 0.5 quart of Nufarm Credit® glyphosate formulation, 50 ppm BMVE and 0.5 quart of Nufarm Credit® glyphosate formulation, 100 ppm BMVE and 0.5 quart of Nufarm Credit® glyphosate formulation, 5 ppm BMVE and 0.75 quart of Nufarm Credit® glyphosate formulation, 50 ppm BMVE and 0.75 quart of Nufarm Credit® glyphosate formulation, 100 ppm BMVE and 0.75 quart of Nufarm Credit® glyphosate formulation, 5 ppm BMVE and 1 quart of Nufarm Credit® glyphosate formulation, 50 ppm BMVE and 1 quart of Nufarm Credit® glyphosate formulation, or 100 ppm BMVE and 1 quart of Nufarm Credit® glyphosate formulation in 5 gallons of water per acre. Eight days after spray application the treated plants were given a rating on a 1 to 5 scale; 1=normal soybean plant development/color, 2=visual stunting of growth and <10% of the leaves exhibiting chlorosis, 3=10 to 50% of the leaves exhibiting chlorosis, 4=>50% of the leaves exhibiting chlorosis, and 5=>50% of the leaves exhibiting chlorosis and senescence. The spray formulations and ratings are listed in Table 15-A. Response of non-Roundup Ready soybeans to bio-regulator formulations eight days following spray application is shown in Table 15-B. NE3001 soybean plants were grown to the sixth trifoliate leaf stage in a greenhouse regime set at 25° C., 14-hour days and 15° C., 10-hour nights and then either not sprayed (control) or sprayed on a spray table set to apply 5, 50, or 100 ppm of BMVE in 5 gallons of water per acre. Application of the bio-regulator BMVE was shown to enhance the activity of glyphosate.

In some embodiments, particular bio-regulators may be particularly effective for enhancing herbicidal activity. For example, in some experiments, at least one of CPTA, COPTA, DIPTA and DCPTA were effective for enhancing herbicidal activity.

TABLE 15-A

| Spray Formulation | Rating |
|---|---|
| 0.05% Tween 20 | 1 |
| 5 ppm BMVE and 0.05% Tween 20 | 1 |
| 50 ppm BMVE and 0.05% Tween 20 | 1 |
| 100 ppm BMVE and 0.05% Tween 20 | 1 |

TABLE 15-A-continued

| Spray Formulation | Rating |
|---|---|
| 0.5 quart of Nufarm Credit ® | 2 |
| 0.75 quart of Nufarm Credit ® | 2 |
| 1 quart of Nufarm Credit ® | 3 |
| 5 ppm BMVE and 0.5 quart of Nufarm Credit ® | 2 |
| 50 ppm BMVE and 0.5 quart of Nufarm Credit ® | 2 |
| 100 ppm BMVE and 0.5 quart of Nufarm Credit ® | 2 |
| 5 ppm BMVE and 0.75 quart of Nufarm Credit ® | 3 |
| 50 ppm BMVE and 0.75 quart of Nufarm Credit ® | 4 |
| 100 ppm BMVE and 0.75 quart of Nufarm Credit ® | 3 |
| 5 ppm BMVE and 1 quart of Nufarm Credit ® | 5 |
| 50 ppm BMVE and 1 quart of Nufarm Credit ® | 5 |
| 100 ppm BMVE and 1 quart of Nufarm Credit ® | 5 |

TABLE 15-B

| | | Height (cm) | Node # | Pod #/ plant | Fresh Pod Weight/ Plant (g) | Dry Pod Weight/ Plant (g) |
|---|---|---|---|---|---|---|
| Control | Mean | 60.7 | 13.8 | 98.0 | 63.5 | 11.9 |
| | Std dev | 3.8 | 0.5 | 9.6 | 12.0 | 2.9 |
| 5 ppm B | Mean | 61.8 | 14.0 | 80.0 | 56.4 | 10.5 |
| | Std dev | 7.7 | 1.2 | 12.1 | 22.9 | 4.6 |
| 50 ppm B | Mean | 64.3 | 13.8 | 91.0 | 55.9 | 9.5 |
| | Std dev | 6.4 | 0.5 | 9.4 | 12.1 | 2.4 |
| 100 ppm B | Mean | 62.7 | 13.5 | 96.3 | 49.9 | 8.7 |
| | Std dev | 7.4 | 1.3 | 9.0 | 7.4 | 2.2 |

Example XVI

In another preferred embodiment of the present invention, the effect of treating Marestail weeds and Velvet Leaf weeds with a bio-regulator according to one embodiment of the present invention were studied. In the study of the Marestail weeds there was a control group that was treated with spray, containing 41% glyphosate, at levels of 1.25 qt/acre. The test group was treated with spray at levels of two gallons per acre, the spray containing 50 ppm of a bio-regulator+1 qt/acre glyphosate. Observations were made at 10 and 16 days after spray application. Marestail weeds were treated twice. After treatments, it was generally observed that the treated group appeared significantly more stressed, had decreased vigor and pigmentation, and reduced biomass.

In the study of the Velvet Leaf weeds, a process similar to the process for Marestail weeds was followed. Velvet Leaf weed test groups were treated with the same formulations and amounts of glyphosate and bio-regulator sprays, and control groups were treated with the same formulation and amount of glyphosate. Again, after treatments, it was generally observed that the treated group appeared significantly more stressed, had decreased vigor and pigmentation, and reduced biomass.

In at least one embodiment, bio-regulators according to embodiments of the present invention may increase the effectiveness of herbicides known in the art. A person skilled in the art may appreciate that use bio-regulation to increase herbicide phytotoxicity may reduce the overall need for herbicide, and thereby reduce the environmental and economic impact of such herbicides.

It is believed that the present invention and many of its attendant advantages will be understood by the foregoing description of embodiments of the present invention, and it will be apparent that various changes may be made in the form, construction, and arrangement of the components thereof without departing from the scope and spirit of the invention or without sacrificing all of its material advantages. The form herein before described being merely an explanatory embodiment thereof, it is the intention of the following claims to encompass and include such changes.

What is claimed is:

1. A composition to be applied to plants and plant seeds comprising:
   an ester of the form

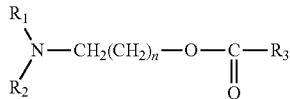

a wetting agent;
   an adjuvant; and
   a herbicide,
   wherein:
   $R_1$ is a lower alkyl group containing between one and six carbon atoms, and a benzyl substituent;
   $R_2$ is a lower alkyl group containing between one and six carbon atoms, and a benzyl substituent;
   $R_3$ is one of a lower alkyl group, cyclopropyl, phenyl and alkyl substituted phenyl;
   n is an integer value from zero to four;
   the ester comprises at least one of 2-(N-Methylbenzylaminoethyl)-2-methylpropanoate (BMBE), 2-(N-Methylbenzylaminoethyl)-3-methylbutanoate (BMVE), 2-(N-Methylbenzylaminoethyl)-2,2-dimethylpropanoate (BMPE), 2-(N-Methylbenzylaminoethyl)-3,3-dimethylbutanoate (BMTE), 2-(N-Methylbenzylaminoethyl)phenylacetate (BMBA), 2-(N-Methylbenzylaminoethyl)phenoxyacetate (BMPA), and 2-(N-Methylbenzylaminoethyl) cylcopropanoate (BMCPA);
   the adjuvant enhances uptake of the ester, sufficient to modify at least one gene expression in a plant; and
   the composition produces a phytotoxic effect in at least one plant.

2. The composition of claim 1, wherein the adjuvant is at least one of B-cyclodextrin and polyoxyethlene (20) sorbitan monooleate.

3. The composition of claim 1, further comprising at least one of polyoxythylene glycol p-isooctylphenylether, chlorothalonil and a mixture of polyalkyleneoxide modified polydimethylsiloxane and polyoxypropylene block polymers.

4. The composition of claim 1, wherein the composition is formulated to modify at least one gene expression in a plant.

5. The composition of claim 1, wherein the composition is formulated to penetrate a seed.

6. A composition to be applied to plants and plant seeds comprising:
   an aqueous solution comprising an ester of the form

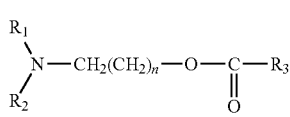

wherein:
   $R_1$ is a lower alkyl group containing between one and six carbon atoms, and a benzyl substituent;
   $R_2$ is a lower alkyl group containing between one and six carbon atoms, and a benzyl substituent;
   $R_3$ is one of a lower alkyl group, cyclopropyl, phenyl and alkyl substituted phenyl;

the ester comprises at least one of 2-(N-Methylbenzylaminoethyl)-2-methylpropanoate (BMBE), 2-(N-Methylbenzylaminoethyl)-3-methylbutanoate (BMVE), 2-(N-Methylbenzylaminoethyl)-2,2-dimethylpropanoate (BMPE), 2-(N-Methylbenzylaminoethyl)-3,3-dimethylbutanoate (BMTE), 2-(N-Methylbenzylaminoethyl)phenylacetate (BMBA), 2-(N-Methylbenzylaminoethyl)phenoxyacetate (BMPA), and 2-(N-Methylbenzylaminoethyl) cylcopropanoate (BMCPA);

n is an integer value from zero to four; and the composition produces a phytotoxic effect on a class of plants.

7. The composition of claim 6, further comprising an adjuvant, wherein the adjuvant is at least one of B-cyclodextrin and polyoxyethlene (20) sorbitan monooleate.

8. The composition of claim 6, further comprising at least one of polyoxythylene glycol p-isooctylphenylether, chlorothalonil and a mixture of polyalkyleneoxide modified polydimethylsiloxane and polyoxypropylene block polymers.

9. The composition of claim 6, wherein the composition is formulated to modify at least one gene expression in a plant.

10. A composition to be applied to plants and plant seeds comprising:

an ester of the form

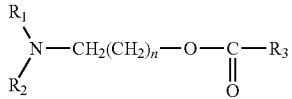

wherein:

R$_1$ is one of a lower alkyl group containing between one and six carbon atoms, and a benzyl substituent;

R$_2$ is one of a lower alkyl group containing between one and six carbon atoms, and a benzyl substituent;

R$_3$ is one of a lower alkyl group, cyclopropyl, phenyl and alkyl substituted phenyl;

the ester comprises at least 2-(N-Methylbenzylaminoethyl)-3-methylbutanoate (BMVE); and n is an integer value from zero to four.

11. The composition of claim 10, wherein the composition comprises 2-(N-Methylbenzylaminoethyl)-2-methylpropanoate (BMBE).

12. The composition of claim 10, wherein the composition comprises 2-(N-Methylbenzylaminoethyl)-2,2-dimethylpropanoate(BMPE).

13. The composition of claim 10, wherein the composition comprises 2-(N-Methylbenzylarninoethyl)-3,3-dimethylbutanoate (BMTE).

14. The composition of claim 10, wherein the composition comprises 2-(N-Methylbenzylaminoethyl)-4-methylbenzoate (BMTA).

15. The composition of claim 10, wherein the composition comprises 2-(N-Methylbenzylarninoethyl)phenylacetate (BMBA).

16. The composition of claim 10, wherein the composition comprises 2-(N-Methylbenzylaminoethyl)phenoxyacetate (BMPA).

17. The composition of claim 10, wherein the composition comprises 2-(N-Methylbenzylaminoethyl)cylcopropanoate (BMCPA).

18. The composition of claim 10, wherein the composition comprises 2-(N-Methylbenzylaminoethyl)-4-bromobenzoate (BMPBA).

19. The composition of claim 10, wherein the composition is formulated to produce a phytotoxic effect in the plant.

* * * * *